United States Patent
Bradbury et al.

(10) Patent No.: US 12,268,742 B2
(45) Date of Patent: Apr. 8, 2025

(54) NANOTHERAPEUTIC SYSTEMS AND METHODS USING PARTICLE-DRIVEN PHOTODYNAMIC THERAPY (PDT)

(71) Applicants: Memorial Sloan Kettering Cancer Center, New York, NY (US); Cornell University, Ithaca, NY (US)

(72) Inventors: Michelle S. Bradbury, New York, NY (US); Ulrich Wiesner, Ithaca, NY (US); Snehal G. Patel, New York, NY (US); Feng Chen, New York, NY (US); Brian Madajewski, New York, NY (US); Daniella Karassawa Zanoni, New York, NY (US)

(73) Assignees: MEMORIAL SLOAN KETTERING CANCER CENTER, New York, NY (US); CORNELL UNIVERSITY, Ithaca, NY (US)

( * ) Notice: Subject to any disclaimer, the term of this patent is extended or adjusted under 35 U.S.C. 154(b) by 957 days.

(21) Appl. No.: 17/051,928

(22) PCT Filed: Apr. 29, 2019

(86) PCT No.: PCT/US2019/029598
§ 371 (c)(1),
(2) Date: Oct. 30, 2020

(87) PCT Pub. No.: WO2019/212945
PCT Pub. Date: Nov. 7, 2019

(65) Prior Publication Data
US 2021/0121569 A1    Apr. 29, 2021

Related U.S. Application Data

(60) Provisional application No. 62/723,044, filed on Aug. 27, 2018, provisional application No. 62/666,086, filed on May 2, 2018.

(51) Int. Cl.
*A61K 41/00* (2020.01)
*A61K 47/69* (2017.01)
*A61K 51/12* (2006.01)

(52) U.S. Cl.
CPC ...... *A61K 41/0057* (2013.01); *A61K 41/0052* (2013.01); *A61K 47/6923* (2017.08); *A61K 47/6929* (2017.08); *A61K 51/1244* (2013.01)

(58) Field of Classification Search
CPC ............ A61K 41/0057; A61K 49/0093; A61K 51/1244; A61K 47/6923; A61K 41/0052
See application file for complete search history.

(56) References Cited

U.S. PATENT DOCUMENTS

| | | | |
|---|---|---|---|
| 8,298,677 | B2 | 10/2012 | Wiesner et al. |
| 9,561,292 | B1 | 2/2017 | Vo-Dinh et al. |
| 2011/0028662 | A1 | 2/2011 | Wiesner et al. |
| 2013/0039848 | A1 | 2/2013 | Bradbury et al. |
| 2014/0248210 | A1 | 9/2014 | Bradbury et al. |
| 2015/0182118 | A1* | 7/2015 | Bradbury ............... A61P 27/02 600/431 |
| 2015/0273084 | A1 | 10/2015 | Kim et al. |
| 2016/0018404 | A1 | 1/2016 | Iyer et al. |
| 2016/0077007 | A1 | 3/2016 | Demos et al. |

FOREIGN PATENT DOCUMENTS

| | | |
|---|---|---|
| CN | 108 675 280 A | 10/2018 |
| WO | WO-2004/067508 A2 | 8/2004 |
| WO | WO-2015/195889 A2 | 12/2015 |
| WO | WO-2016/061256 A1 | 4/2016 |
| WO | WO-2016/196201 A1 | 12/2016 |
| WO | WO-2017/189961 A1 | 11/2017 |
| WO | WO-2018/191316 A1 | 10/2018 |
| WO | WO-2019/213458 A1 | 11/2019 |

OTHER PUBLICATIONS

Han, R. et al., pH-Responsive frug release and NIR-triggered singlet oxygen generation based on a multifunctional core-shell-shell structure, Physical Chemistry Chemical Physics, 18 (2016) 25497-25503. ("Han") (Year: 2016).*
Cen, Y. et al., Core-Shell-Shell Multifunctional Nanoplatform for Intracellular Tumor-Related mRNAs Imaging and Near-Infrared Light Triggered Photodynamic-Photothermal Synergistic Therapy, Analytical Chemistry, 89(19):10321-10328, (2017).
Fan, W. et al., A smart upconversion-based mesoporous silica nanotheranostic system for synergetic chemo-/radio-/photodynamic therapy and simultaneous MR/UCL imaging, Biomaterials, 35(32):8992-9002, (2014).
Ge, J. et al., Carbon Dots with Intrinsic Theranostic Properties for Bioimaging, Red-Light-Triggered Photodynamic/Photothermal Simultaneous Therapy In Vitro and In Vivo, Advanced Healthcare Materials, 5(6):665-675, (2016).
Guo, W. et al., Ti0 2-x Based Nanoplatform for Bimodal Cancer Imaging and NIR-Triggered Chem/Photodynamic/Photothermal Combination Therapy, Chemistry of Materials, 29(21):9262-9274, (2017).
Han, R. et al., pH-Responsive drug release and NIR-triggered singlet oxygen generation based on a multifunctional core-shell-shell structure, Physical Chemistry Chemical Physics, 18*36):25497-25503, (2016).
He, X. et al., Mehtylene blue-encapsulated phosphonate-terminated silica nanoparticles for simultaneous in vivo imaging and photodynamic therapy, Biomaterials, 30(29):5601-5609, (2009).
https://en.wikipedia.org/wiki/Leukoplakia.

(Continued)

*Primary Examiner* — Deanna K Hall
(74) *Attorney, Agent, or Firm* — ArentFox Schiff LLP; Daniel W. Clarke

(57) ABSTRACT

Described herein are systems and methods for particle-based photodynamic therapy (PDT) for the treatment of diseases such as cancer of the oral cavity and/or ovarian cancer metastases along the lining of the pelvis. The technology includes an imaging system (e.g., a multichannel imaging camera) configured to perform diagnostic and/or therapeutic treatment on diseased tissue. In certain embodiments, the imaging system comprises one or more excitation sources (e.g., one or more lasers) to assess and/or treat diseased tissue.

25 Claims, 15 Drawing Sheets

(56) References Cited

OTHER PUBLICATIONS

Huang, P. et al., Light Triggered Theranostics Based on Phtosensitizer-Conugated Carbon Dots for Simultaneous Enhanced-Fluorescence Imaging and Photodynamic Therapy, Advanced Materials, 24(37):5104-5110, (2012).

International Search Report PCT/US2019/30495 filed May 2, 2019, 3 pages, (Sep. 3, 2019).

International Search Report, PCT/US2019/029598 (Nanotherapeutic Systems and Methods Using Particle-Driven Photodynamic Therapy (PDT), filed Apr. 20, 2019), issued by ISA/European Patent Office, 11 pages, Sep. 25, 2019.

Kofler, B. et al., Photodynamic Effect of Methylene Blue and Low Level Laser Radiation in Head and Neck Squamous Cell Carcinoma Cell Lines, International Journal of Molecular Sicences, 19(4):1107, (2018).

Kohle, F.F.E., et al., Amorphous Quantum Nanomaterials, Advanced Materials, 1-9, (2018).

Li, Songying, Thesis: Functionalized SUB-10 Nm Silica Methylene Blue Nanophotosensitizers, In: Functionalized Sub-10 nm Silica Methylene Blue Nanophtosensitizers, 42 pages, (2018).

Ma, K. et al., Control of Ultrasmall Sub-10 nm Ligand-Functionalized Fluorescent Core-Shell Silica Nanoparticle Growth in Water, Chemistry of Materials, 27(11):4119-4133, (2015).

Ma, K., and Wiesner, U., Modular and orthogonal post-PEGylation surface modifications by insertion enabling penta-functional ultrasmall organic-silica hybrid nanoparticles, Chemistry of Materials, 29(16):6840-6855, (2017).

Oliveira, T.L., et al., HPLC-FLD methods to quantify chloroaluminium phthalocyanine in nanoparticles, plasma and tissue: application in pharmacokinetic and biodistribution studies, Journal of Pharmaceutical and Biomedical Analysis, 56(1): 70-71, (2011).

Partial Search Report, International Application No. PCT/US2019/029598 (Nanotherapeutic Systems and Methods Using Particle-Driven Photodynamic Therapy (PDT), filed Apr. 29, 2019), issued by ISA/European Patent Office, 7 pages, Aug. 2, 2019.

Provisional Opinion Accompanying Partial Search Report, International Application No. PCT/US2019/029598 (Nanotherapeutic Systems and Methods Using Particle-Driven Photodynamic Therapy (PDT), filed Apr. 29, 2019), issued by ISA/European Patent Office, 11 pages, Aug. 2, 2019.

Seo, S. et al., NIR-light-induced surface-enhanced Raman scattering for detection and photothermalphotodynamic therapy of cancer cells using methylene blue-embedded gold nanorod@SiO2nanocomposites, Biomaterials, 35(10):3309-3318, (2014).

U.S. Appl. No. 62/666,086 entitled "Functionalized Sub-10 nm Silica Nanophotosensitizers," filed on May 4, 2018, the disclosure of which is hereby incorporated by reference in its entirety for more information on the nanoparticle composition technology.

Wang, X. et al., A Reactive $^1O_2$—Responsive Combined Treatment System of Photodynamic and Chemotherapy for Cancer, Scientific Reports, 6(1):2911-1, (2016).

Written Opinion, PCT/US2019/029598 (Nanotherapeutic Systems and Methods Using Particle-Driven Photodynamic Therapy (PDT), filed Apr. 20, 2019), issued by ISA/European Patent Office, 16 pages, Sep. 25, 2019.

Yang, G. et al., Smart Nanoreactors for pH-Responsive Tumor Homing, Mitochondria-Targeting, and Enhanced Photodynamic-Immunotherapy of Cancer, Nano Letters, 18(4):2475-2484, (2018), with supporting information (13 pages).

* cited by examiner

Beam size: 7-8 mm

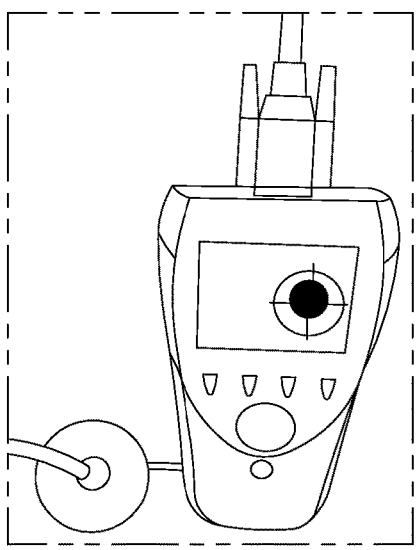

| Beam diameter size (mm) | 8 |
|---|---|
| Beam area ( cm2) | 0.5024 |
| | |
| Power Density (mW/cm2) | Power (mW) |
| 1 | 0.5024 |
| 2 | 2.512 |
| 10 | 5.024 |
| 100 | 50.24 |
| 250 | 125.6 |
| 500 | 251.2 |
| 1000 | 502.4 |
| 1500 | 753.6 |
| 2000 | 1004.8 |
| 2500 | 1256 |
| 3000 | 1507.2 |
| 3500 | 1758.4 |
| 4000 | 2009.6 |
| 4500 | 2260.8 |

Product Datasheet

---

LRD-655 Collimated Diode Laser System

Part Number: D6550B5FX

Similar Products:
For information about the other lasers in this product family visit:
http:/www.laserglow.com/D65

Ordering:
Order Online Now or Request Quote:
http:/www.laserglow.com/D6550B5FX

Series Specifications:

| Nominal Wavelength | 655 nm |
|---|---|
| Output Type | CW |
| Laser Source Type | Diode |

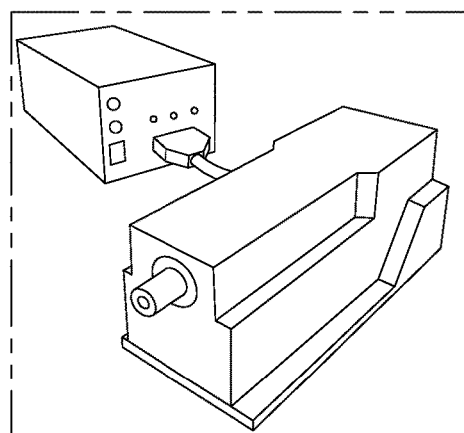

FIG. 1A 655 nm laser

Product Datasheet

LRD-655 Collimated Diode Laser System

Part Number: D6550B5FX

Similar Products:
For information about the other lasers in this product family visit:
http://www.laserglow.com/D65

Ordering:
Order Online Now or Request Quote:
http://www.laserglow.com/D6550B5FX

Series Specifications:

| Nominal Wavelength | 655 nm |
|---|---|
| Output Type | CW |
| Laser Source Type | Diode |

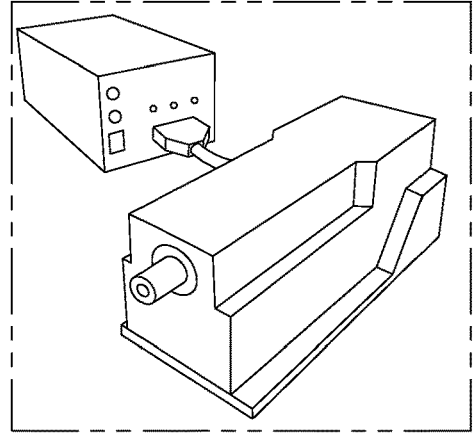

Beam Tracker

10A-PPS

| 10A-PPS* Low power |
|---|
| Power / Energy / Position / Size |
| Broadband |
| 0.19 - 20 |
| Ø16mm |
| 20mW - 10W |
| 10W / 5W / 0.5W |
| 1mW |
| NA |
| 28 |
| 0.8 |
| 3 |
| 1 |
| 6mJ - 2J |
| 2J / 200mJ |
| 6mJ |

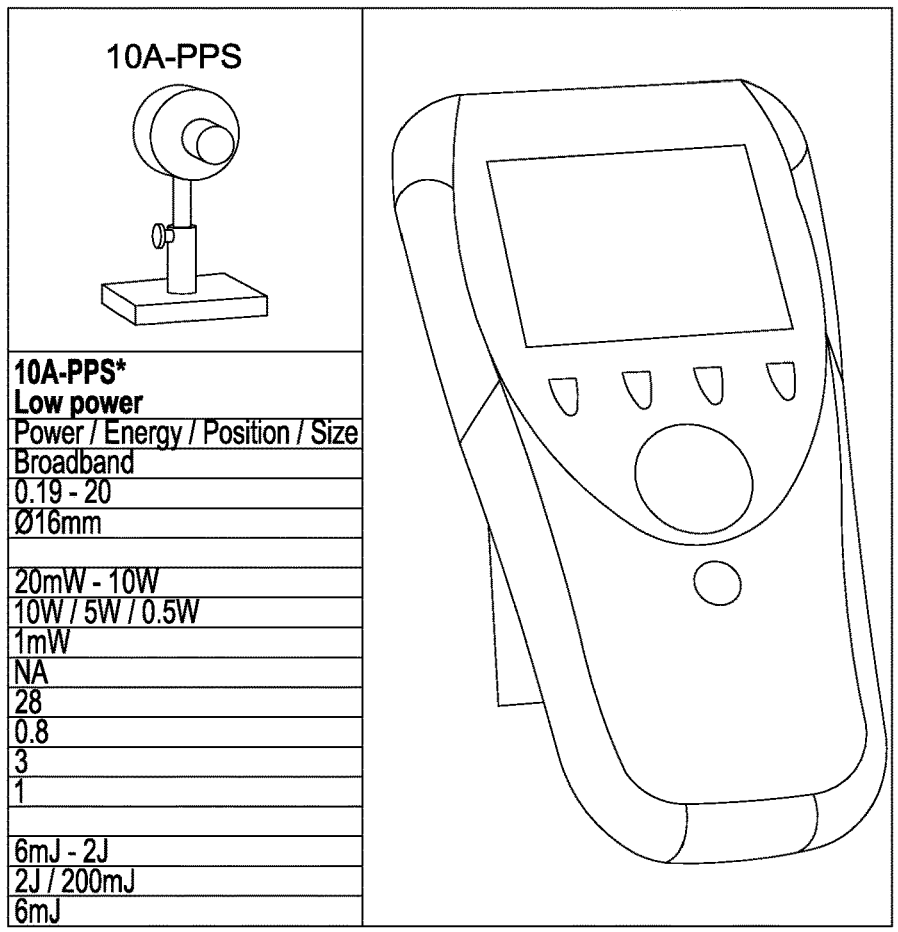

FIG. 1B

| | |
|---|---|
| Beam diameter size (mm) | 10 |
| Beam area (cm2) | 0.785 |
| Power Density (mW/cm2) | Power (mW) |
| 1 | 0.785 |
| 5 | 3.925 |
| 10 | 7.85 |
| 50 | 39.25 |
| 100 | 78.5 |
| 500 | 392.5 |
| 1000 | 785 |
| 1500 | 1177.5 |
| 2000 | 1570 |
| 2500 | 1962.5 |
| 3000 | 2355 |
| 3500 | 2747.5 |
| 4000 | 3140 |
| 4500 | 3532.5 |
| 5000 | 3925 |

FIG. 3

Chemical Structures

Molecular formula: $C_{27}H_{19}Cl_3O_8$
Molecular weight: 577.8013
CAS name/number:

Fluorescence spectra

Ex: 495 nm

Em: 520nm

```
┌─────────────────────────────────────────────────────────────┐
│ Administering to a tissue (e.g., a diseased tissue) of a subject a │
│ first composition comprising nanoparticles, wherein the     │
│ nanoparticles comprise a PDT-active moiety                  │
└─────────────────────────────────────────────────────────────┘
                              │
                              ▼
┌─────────────────────────────────────────────────────────────┐
│ Administering to the tissue of the subject a second composition │
│ comprising a PTT-active moiety                              │
└─────────────────────────────────────────────────────────────┘
                              │
                              ▼
┌─────────────────────────────────────────────────────────────┐
│ Directing excitation light onto the tissue of the subject to activate │
│ the PDT-active moiety, and                                  │
│ optionally directing excitation light having a wavelength in a │
│ range from about 700 nm to about 1 mm onto the tissue of the │
│ subject to activate the PTT-active moiety                   │
└─────────────────────────────────────────────────────────────┘
                              │
                              ▼
┌─────────────────────────────────────────────────────────────┐
│ Detecting a signal emitted by the first composition         │
└─────────────────────────────────────────────────────────────┘
```

FIG. 12

A device (e.g., one or more lasers, e.g., a multichannel camera) for performing a nanotherapeutic method using particle-driven photodynamic therapy (PDT)

FIG. 14

NANOTHERAPEUTIC SYSTEMS AND METHODS USING PARTICLE-DRIVEN PHOTODYNAMIC THERAPY (PDT)

CROSS-REFERENCE TO RELATED APPLICATION

This application is a 371 National Stage entry of International Application No. PCT/US2019/029598, which claims the benefit of U.S. Patent application Ser. No. 62/666,086 filed on May 2, 2018 and U.S. Patent application Ser. No. 62/723,044 filed on Aug. 27, 2018, the disclosures of each of which are hereby incorporated by reference in their entireties.

FIELD OF THE INVENTION

This invention relates generally to systems and methods for particle-driven photodynamic therapy (PDT) (e.g., using nanoparticles having a diameter less than 20 nm). In certain embodiments, the invention relates to therapy that combines PDT with immunotherapy, ferroptosis, radiotherapy, and/or photothermal therapy (PTT).

BACKGROUND

Photodynamic therapy (PDT) provides an alternative non-invasive therapeutic approach for the treatment of diseases such as cancer. PDT is a treatment that uses a photosensitizer agent and a particular type of light. When the photosensitizer agent is exposed to a specific wavelength of light, the photosensitizer agent produces a form of oxygen that kills nearby cells.

For example, in cancer treatment, a photosensitizer agent is administered into the bloodstream of a subject, or is administered as a topical, intraperitoneal, or intracavitary agent to the subject. The agent can be absorbed by all cells in the body, but stays in cancer cells longer than healthy cells. After a time period (e.g., 2-3 days) following the administration of the photosensitizer agent, the cancer cells are exposed to light. The photosensitizer agent in the cancer cells absorbs the light and produces an active form of oxygen (called an oxygen singlet) that destroys the cancer cells.

PDT currently suffers from a variety of challenges. For example, the light needed to activate most photosensitizer agents cannot pass through more than about one-third of an inch of tissue. Therefore, PDT is typically limited to treat tumors on or just under the skin or lining the walls of internal organs or cavities. PDT is also less effective in treating large tumors because the light cannot penetrate deeply into the tumors.

Alternative treatments for cancers beyond the reach of PDT include radiotherapy and immune checkpoint inhibitors, which can lead to dramatic and sustained therapeutic responses in the treatment of poorly prognostic tumors. However, responses to radiotherapy or these inhibitors may be associated with off-target toxicities and potentially fatal immune-related adverse events, in addition to their restricted application to small patient cohorts.

Thus, there remains a need for other compositions and protocols for the treatment of such tumors.

SUMMARY

Described herein are systems and methods for particle-based photodynamic therapy (PDT) for treatment of diseases such as cancer of the oral cavity (e.g., tongue cancer), aerodigestive tract malignancies, and/or solid ovarian cancer metastases along the lining of the pelvis. The technology includes an imaging system (e.g., a multichannel imaging camera) configured to perform diagnostic and/or therapeutic treatment of diseased tissue. In certain embodiments, the imaging system comprises one or more excitation sources (e.g., one or more lasers, e.g., a multichannel imaging system) to assess and/or treat diseased tissue (e.g., in a small affected area such as the oral cavity).

In certain embodiments, the technology also involves nanoparticle compositions that comprise a PDT-active moiety (e.g., Cy5, e.g., methylene blue, e.g., Cy5.5) associated (e.g., covalently bound, e.g., non-covalently bound) with silica-based nanoparticles.

In certain embodiments, the fluorophore moiety is Cy5, i.e. Cyanine 5:

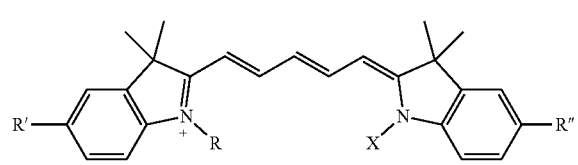

wherein R is —CH₃, R' is —H, R" is —H, and X is —(CH₂)₅—C(O)—, or any suitable salt thereof. In certain embodiments, either or both of R' and R" is —S(O)₂—OH or a suitable sulfonate (i.e. —S(O)₂—O⁻) salt thereof. Cy5 can be associated with the described nanoparticle compositions using any suitable means, e.g., conjugation via an activated form of the acid (X is —(CH₂)₅—C(O)—OH) such as the NHS ester, which can be purchased or can be made using N-hydroxysuccinimide. Other forms of Cy5 can be used in accordance with the systems and methods described by the present disclosure, e.g., equivalents and/or analogues thereof (e.g., any of the foregoing wherein R is —CH₂CH₃), associated with the described nanoparticle compositions.

In certain embodiments, the fluorophore moiety is Cy5.5, i.e. Cyanine 5.5:

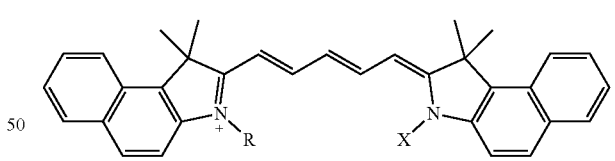

wherein R is —CH₃ and X is —(CH₂)₅—C(O)—, or any suitable salt thereof. Cy5.5 can be associated with the described nanoparticle compositions using any suitable means, e.g., conjugation via an activated form of the acid (X is —(CH₂)₅—C(O)—OH) such as the NHS ester, which can be purchased or can be made using N-hydroxysuccinimide. Other forms of Cy5.5 can be used in accordance with the systems and methods described by the present disclosure, e.g., equivalents and/or analogues thereof (e.g., R is —CH₂CH₃), associated with the described nanoparticle compositions.

In certain embodiments, the fluorophore is methylene blue or 3,7-Bis(dimethylamino)phenothiazin-5-ium chloride. In certain embodiments, the fluorophore comprises:

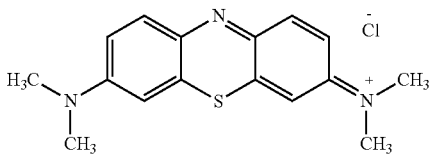

Methylene blue (MB) can be associated with the described nanoparticle compositions using any suitable means, e.g., conjugation via an activated form of the acid (X is —$(CH_2)_5$—C(O)—OH) such as the NHS ester, which can be purchased or can be made using N-hydroxysuccinimide. Other forms of methylene blue can be used in accordance with the systems and methods described by the present disclosure, e.g., equivalents and/or analogues thereof, associated with the described nanoparticle compositions.

In certain embodiments, the nanoparticle compositions are those described by Kohle et al. in U.S. Provisional Application No. 62/666,086 entitled "Functionalized Sub-10 nm Silica Nanophotosensitizers," filed on May 2, 2018, the disclosure of which is hereby incorporated by reference in its entirety. In certain embodiments, the nanoparticles are described by Kohle et al. in "Amorphous Quantum Nanomaterials" first published on Dec. 5, 2018 in Advanced Materials, the disclosure of which is hereby incorporated by reference in its entirety.

These nanoparticle compositions are found to be surprisingly excellent generators of singlet oxygen, which is associated with high cancer cell kill efficiency. Furthermore, attaching a PDT-active moiety to an ultrasmall nanoparticle offers advantages (e.g., average overall particle diameter, with attached PDT-active moiety, no greater than 20 nm, e.g., no greater than 15 nm, e.g., no great than 10 nm), such advantages including the ability to track/visualize the nanoparticle composition (while retaining renal clearance of the nanoparticle), improved localization of the nanoparticle composition, e.g., at locations requiring treatment, the ability to achieve higher local concentrations or reactive oxygen species (ROS) generation at areas requiring treatment, the ability to circumvent immune evasion/immunomodulatory mechanisms employed by tumors, the ability to increase tumor immunogenicity to elicit a multi-antigen vaccination effect without the need for a priori knowledge of tumor antigens, and the ability to modulate tumor microenvironment.

A nanoparticle composition can comprise various amounts of PDT-active moieties. Without wishing to be bound to any theory, it is considered that the number of PDT-active moieties associated to the nanoparticle composition correlates to the amount of PDT-active moieties precursor used in the synthesis of the nanoparticle compositions. For example, for nanoparticles having a diameter below 10 nm, such nanoparticles may have on average from about 1 to about 20 (e.g., from about 1 to about 10, e.g., from about 1 to about 5, e.g., from about 1 to about 2) PDT-active moieties per nanoparticle composition.

The nanotherapeutic systems and methods described herein may be tuned by varying the power density of the laser that is directed onto the tissue of the subject, the beam diameter of the laser used, the illumination time of the laser on the tissue of the subject, and/or the fluorophore dye type and concentration of the nanoparticle composition used for PDT treatment. For example, a range of usable power densities and beam diameters of a laser can be determined by directing the laser onto control (healthy) cells to ensure minimal cell death to surrounding healthy tissue, and by experimenting with diseased cells to ensure satisfactory cell death. This protocol can be used to adjust the variables suitable for different cell types, tumor types, tumor burden, tumor location, and type of PDT-active moiety (e.g., fluorophore) that is used in accordance with the embodiments of the present disclosure. Further, the PDT treatment may be combined with ferroptosis, immunotherapy, radiotherapy, and/or photothermal therapy (PTT), as discussed in more detail herein.

In certain embodiments, the technology also involves nanoparticle compositions that comprise nanosensors such as those described by Bradbury et al., International Application No. PCT/US18/38973 entitled "Systems and Methods for Super-Resolution Optical Imaging Technologies and/or Nanosensor-Driven Patient Monitoring and/or Treatment," filed on Jun. 22, 2018, the contents of which is hereby incorporated by reference in its entirety, the disclosure of which is hereby incorporated by reference in its entirety. The nanosensors provide sensor-driven readout (e.g., displayed as a ROS image and/or map) of ROS detected in a tissue of the subject. The image and/or map of ROS detected by the nanosensors serves as a mechanism to guide treatment and/or assessment of diseased tissue.

The nanoparticle compositions can also be administered as part of a combination therapy, where particle-driven PDT is supplemented by one or more other therapies such as ferroptosis, immunotherapy, radiotherapy, and/or photothermal therapy (PTT). For example, one or more of the other therapies are delivered by the nanoparticle compositions, e.g., by the same or different nanoparticles with attached PDT-active moieties. As another example, one or more of the other therapies are delivered by a second composition in addition to the nanoparticles with attached PDT-active moieties.

For instance, when the technology is used in combination with a second composition comprising immune checkpoint inhibitors, the resulting immunostimulatory effects of PDT-inducing, functionalized nanoparticles may provide a variety of benefits such as (1) eliciting immunogenic cell death (ICD) (e.g., via ferroptosis or apoptosis), (2) improving antigen presentation, (3) achieving effective eradication of tumors, (4) preventing relapse, and/or (5) triggering antitumor responses against disease dissemination. As such, the described combination approaches of targeting tumor cells, antigen presenting cells (APCs), and T cells can convert a non-responsive tumor to a responsive one.

These improvements may result in fewer PDT treatment sessions necessary and/or reduced exposure to PDT laser needed for effective treatment of the tumor. Furthermore, it is found that these nanoparticle compositions can be effectively applied topically, which is beneficial for treatment of various aerodigestive and/or oral cancers and/or intravenously injected, which is beneficial for treatment of various solid ovarian tumor metastases along the tissue lining of the pelvis.

Furthermore, compared to conventional treatment methods, the nanoparticle compositions have an additional advantage of being visually detectable, e.g., via a multichannel imaging camera, or by unaided sight, under certain conditions. In certain embodiments, detection of the nanoparticle compositions is achieved using a multichannel imaging camera as described by Bradbury et al. US Publication No. US 2015/0182118 A1, "Systems, Methods, and Apparatus for Multichannel Imaging of Fluorescent Sources in Real Time", the disclosure of which is hereby incorporated by reference in its entirety. For example, the multichannel imaging camera is capable of simultaneously imaging, in real-time, different fluorescent sources within a subject using a portable multichannel fluorescent camera. The multichannel imaging camera can be a portable imaging system that is capable of detecting light from multiple probes species simultaneously with high signal-to-noise ratio. Such a system offers advantages over pre-existing systems that cannot simultaneously detect and distinguish more than one fluorescent probe species in real-time. In addition, the multichannel imaging camera can be used for simultaneous imaging and treatment of diseased tissue.

The ability to visualize the nanoparticle composition further allows more effective concentration of the PDT-active moiety at locations that will offer the most benefit, and more efficient application of laser energy, e.g., such that laser energy can be applied only where the nanoparticle composition is located.

Systems described herein include a laser that can be used, for example, both for imaging and PDT treatment, e.g., along with power adjustment depending on whether the system is in imaging or treatment mode. In certain embodiments, a separate treatment laser and imaging laser can be used. For example, an IR camera can be used to generate a temperature map of an area of treatment (and its surroundings) in addition to the laser that performs PDT.

The imaging systems and methods also provide both static and functional assessments of an area of treatment (and its surroundings). For example, functional assessments can include measurements of ROS, oxygenation, perfusion, etc. Static and functional assessments may inform subsequent treatment and/or an overall treatment plan. In particular, the nanoparticle compositions described herein provide over 100-times better (e.g., 600-times better) oxygen generation, thereby offering much higher cancer kill rates. The high efficiency of the nanoparticle compositions can reduce the number of PDT treatment sessions needed, and can reduce the treatment time (time of exposure to laser treatment) for each session. Moreover, imaging at one session can be used to determine treatment during subsequent session(s).

In one aspect, the invention is directed to a nanotherapeutic method using particle-driven photodynamic therapy (PDT), the method comprising: (a) administering to a tissue (e.g., a diseased tissue) of a subject a first composition comprising nanoparticles, wherein the nanoparticles comprise: (i) a PDT-active moiety, and (b) directing (e.g., via a first laser, e.g., via a multichannel imaging system) excitation light onto the tissue of the subject to activate the PDT-active moiety (e.g., wherein the excitation light is directed onto the tissue of the subject at a power density within a determined range (e.g., for therapy) (e.g., wherein the range has a minimum of at least 100 W/cm$^2$ or at least 500 W/cm$^2$ or at least 1000 W/cm$^2$ or at least 2000 W/cm$^2$, or at least 5000 W/cm$^2$)) [e.g., directing light onto the tissue of the subject for a determined range of time (e.g., for less than 120 minutes, e.g., for less than 100 minutes, e.g., for less than 60 minutes, e.g., for less than 30 minutes, e.g., for less than 20 minutes, e.g., for less than 15 minutes, e.g., for less than 10 minutes)]; and (c) detecting (e.g., visually) (e.g., via the multichannel imaging system, e.g., via unaided sight, under certain conditions) a signal emitted by the first composition [e.g., for static and/or functional assessment(s) of the tissue (and its surroundings), e.g., wherein the assessment(s) comprise assessment of reactive oxygen species (ROS) oxygenation levels (e.g., using nanosensors, e.g., ROS-detecting nanosensors), perfusion, etc., e.g., wherein the assessment(s) comprise detection of location and/or concentration of PDT-active moiety in/on the tissue].

In certain embodiments, the PDT-active moiety comprises a PDT-photosensitive agent. In certain embodiments, the PDT-photosensitive agent comprises a fluorophore. In certain embodiments, the PDT-photosensitive agent comprises methylene blue. In certain embodiments, the PDT-photosensitive agent comprises Cy5. In certain embodiments, the PDT-active moiety absorbs electromagnetic radiation (emr) having a wavelength within a range from about 600 nm to about 700 nm, e.g., 660 nm (e.g., for methylene blue), e.g., from about 650 nm to about 654 nm (e.g., for Cy5).

In certain embodiments, the first composition comprises a reactive oxygen species (ROS) generator.

In certain embodiments, the method comprises administering the first composition to the tissue of the subject for accumulation at sufficiently high concentrations in the tissue to induce ferroptosis (e.g., in the presence the excitation light) (e.g., for combination therapy).

In certain embodiments, the first composition is administered as a topical, subdermal, peritumoral, oral, intravenous, nasal, subcutaneous, intramuscular, intratumoral, intraperitoneal (IP), intracavitary, or transdermal composition.

In certain embodiments, the method comprises administering (e.g., systemically) to the tissue of the subject a second composition comprising a drug (e.g., an immune adjuvant, e.g., an immunomodulator, e.g., an immune checkpoint inhibitor) (e.g., for combinatorial therapy) (e.g., thereby treating two or more lesions) (e.g., to induce ferroptosis).

In certain embodiments, the first composition comprises an immune adjuvant (e.g., an antibody fragment, e.g., a toll-like receptor agonist) (e.g., a targeting agent) [e.g., thereby causing immunogenic cell death (ICD) (e.g., via ferroptosis, e.g., via apoptosis)] (e.g., thereby improving antigen presentation, e.g., thereby substantially eradicating tumors, e.g., thereby preventing disease relapse).

In certain embodiments, the tissue comprises squamous cells in the oral cavity (e.g., wherein the tissue comprises tongue tissue, e.g., wherein the tissue comprises cheek tissue, e.g., wherein the tissue comprises other tissue in the oral cavity).

In certain embodiments, the subject is suffering from or susceptible to oral cancer and/or residual disease of the oral cavity (e.g., wherein the oral cancer and/or residual disease is or comprises leukoplakia).

In certain embodiments, the tissue comprises tissue in the pelvis (e.g., solid ovarian tumor has metastasized to the lining of the pelvis).

In certain embodiments, the subject is suffering from and/or susceptible to a gynecological malignancy. In certain embodiments, the gynecological malignancy comprises ovarian cancer (e.g., metastatic ovarian cancer) (e.g., along the lining of the pelvis). In certain embodiments, the gynecological malignancy comprises uterine cancer.

In certain embodiments, the gynecological malignancy comprises cervical cancer. In certain embodiments, the tissue comprises tissue in the aerodigestive tract (e.g., lips, mouth, tongue, nose, throat, vocal cords, and part of the esophagus and windpipe) (e.g., wherein the subject is suffering from and/or susceptible to aerodigestive tract malignancies).

In certain embodiments, the tissue comprises a member selected from the group consisting of the mouth tissue, gastrointestinal tract tissue, urinary tract tissue, and genital tissue (e.g., wherein the subject is suffering from and/or susceptible to leukoplakia).

In certain embodiments, the method comprises a theranostic method (e.g., wherein the detecting step is configured to perform diagnostics and/or therapeutic treatment on the tissue of the subject (e.g., wherein the diagnostics and therapeutic treatment can combine with other treatments, e.g., for combinatorial treatment)).

In certain embodiments, the excitation light that is directed onto the tissue for treatment is directed at a higher power density than the excitation light that is directed onto the tissue for diagnostics. In certain embodiments, the excitation light is directed onto the tissue of the subject via a multichannel camera system for both imaging and PDT treatment (e.g., with power adjustment depending on whether the camera is in imaging or treatment mode).

In certain embodiments, the first laser treats the tissue of the subject, and a second laser detects (e.g., visually) (e.g., via the multichannel imaging system, e.g., via unaided sight, under certain conditions) the signal emitted by the first composition.

In certain embodiments, the first composition comprises: (ii) a first PTT-active moiety [e.g., wherein the PTT-active moiety absorbs emr having a wavelength longer than the wavelength of the emr absorbed by the PDT-active moiety (e.g., at a range from about 700 nm to about 900 nm, e.g., 800 nm)] (e.g., wherein the PTT-active moiety comprises a PTT-photosensitive agent, e.g., a metal, e.g., a gold nanoparticle).

In certain embodiments, the method comprises administering to the tissue of the subject a third composition comprising a second PTT-active moiety (e.g., a PTT-photosensitive agent, e.g., a metal, e.g., a gold nanoparticle) (e.g., for combinatorial therapy) (e.g., thereby treating two or more lesions).

In certain embodiments, the method comprises directing (e.g., via a third laser, e.g., via a multichannel imaging system) excitation light having a wavelength in a range from about 700 nm to about 1 mm (e.g., an infrared wavelength range) onto the tissue of the subject, thereby treating the tissue with photothermal therapy (PTT).

In certain embodiments, the method comprises administering radiotherapy to the tissue of the subject. In certain embodiments, the radiotherapy comprises administering a radiotherapeutic composition to the tissue, e.g., via topical application.

In certain embodiments, the first composition comprises a radiolabel (e.g., associated with each of the nanoparticles). In certain embodiments, the radiolabel comprises a member selected from the group consisting of $^{99m}Tc$, $^{111}In$, $^{64}Cu$, $^{67}Ga$, $^{186}Re$, $^{188}Re$, $^{153}Sm$, $^{177}Lu$, $^{67}Cu$, $^{123}I$, $^{124}I$, $^{125}I$, $^{11}C$, $^{13}N$, $^{15}O$, $^{18}F$, $^{186}Re$, $^{188}Re$, $^{153}Sm$, $^{166}Ho$, $^{177}Lu$, $^{149}Pm$, $^{90}Y$, $^{213}Bi$, $^{103}Pd$, $^{109}Pd$, $^{159}Gd$, $^{140}La$, $^{198}Au$, $^{199}Au$, $^{169}Yb$, $^{175}Yb$, $^{165}Dy$, $^{166}Dy$, $^{67}Cu$, $^{105}Rh$, $^{111}Ag$, $^{89}Zr$, $^{225}Ac$, and $^{192}Ir$.

In certain embodiments, the nanoparticles are silica-based. In certain embodiments, the nanoparticles comprise: a silica-based core; a fluorescent compound within the core; a silica shell surrounding at least a portion of the core; and an organic polymer attached to the nanoparticle, thereby coating the nanoparticle.

In certain embodiments, the nanoparticles have an average diameter no greater than about 50 nm. In certain embodiments, the nanoparticles have an average diameter no greater than 20 nm. In certain embodiments, the nanoparticles have an average diameter from about 5 nm to about 7 nm.

In certain embodiments, the nanoparticles comprise a member selected from the group consisting of C dots, C' dots, srC' dots, iC' dots, and MB-C' dots.

In certain embodiments, the first composition comprises from 1 to 100 targeting moieties attached to each of the nanoparticles, wherein the targeting moieties bind to receptors on tumor cells. In certain embodiments, the first composition comprises from 1 to 100 ligands (e.g., wherein each of the ligands comprises an immunomodulator) attached to each of the nanoparticles.

In certain embodiments, the first composition comprises a drug attached to each of the nanoparticles. In certain embodiments, the drug is attached via a linker moiety.

In certain embodiments, the first composition comprises a reactive oxygen species (ROS) sensor.

In another aspect, the invention is directed to a device (e.g., one or more lasers, e.g., a multichannel camera) for performing any one of the methods described herein.

Elements of embodiments involving one aspect of the invention (e.g., methods) can be applied in embodiments involving other aspects of the invention (e.g., systems), and vice versa.

Definitions

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Administration": The term "administration" refers to introducing a substance into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments. In certain embodiments, administration is oral. Additionally or alternatively, in certain embodiments, administration is parenteral. In certain embodiments, administration is intravenous.

"Antibody": As used herein, the term "antibody" refers to a polypeptide that includes canonical immunoglobulin sequence elements sufficient to confer specific binding to a particular target antigen. Intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH)

domain (located at the tips of the Y structure), followed by three constant domains: $CH_1$, $CH_2$, and the carboxy-terminal $CH_3$ (located at the base of the Y's stem). A short region, known as the "switch", connects the heavy chain variable and constant regions. The "hinge" connects $CH_2$ and $CH_3$ domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the $CH_2$ domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. Affinity and/or other binding attributes of Fc regions for Fc receptors can be modulated through glycosylation or other modification. In certain embodiments, antibodies produced and/or utilized in accordance with the present invention include glycosylated Fc domains, including Fc domains with modified or engineered such glycosylation. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In certain embodiments, an antibody is polyclonal; in certain embodiments, an antibody is monoclonal. In certain embodiments, an antibody has constant region sequences that are characteristic of mouse, rabbit, primate, or human antibodies. In certain embodiments, antibody sequence elements are humanized, primatized, chimeric, etc, as is known in the art. Moreover, the term "antibody" as used herein, can refer in appropriate embodiments (unless otherwise stated or clear from context) to any of the art-known or developed constructs or formats for utilizing antibody structural and functional features in alternative presentation. For example, embodiments, an antibody utilized in accordance with the present invention is in a format selected from, but not limited to, intact IgG, IgE and IgM, bi- or multi-specific antibodies (e.g., Zybodies®, etc), single chain Fvs, polypeptide-Fc fusions, Fabs, cameloid antibodies, masked antibodies (e.g., Probodies®), Small Modular ImmunoPharmaceuticals ("SMIPs™"), single chain or Tandem diabodies (TandAb®), VHHs, Anticalins®, Nanobodies®, minibodies, BiTE®s, ankyrin repeat proteins or DARPINs®, Avimers®, a DART, a TCR-like antibody, Adnectins®, Affilins®, Trans-bodies®, Affibodies®, a TrimerX®, MicroProteins, Fynomers®, Centyrins®, and a KALBITOR®. In certain embodiments, an antibody may lack a covalent modification (e.g., attachment of a glycan) that it would have if produced naturally. In certain embodiments, an antibody may contain a covalent modification (e.g., attachment of a glycan, a payload [e.g., a detectable moiety, a therapeutic moiety, a catalytic moiety, etc], or other pendant group [e.g., poly-ethylene glycol, etc.]).

"Antibody fragment": As used herein, an "antibody fragment" includes a portion of an intact antibody, such as, for example, the antigen-binding or variable region of an antibody. In certain embodiments, the nanoparticle compositions described herein comprise, have attached, and/or have associated therewith one or more antibodies and/or one or more antibody fragments. Examples of antibody fragments include Fab, Fab', F(ab')2, and Fv fragments; triabodies; tetrabodies; linear antibodies; single-chain antibody molecules; and multi specific antibodies formed from antibody fragments. For example, antibody fragments include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region. In many embodiments, an antibody fragment contains sufficient sequence of the parent antibody of which it is a fragment that it binds to the same antigen as does the parent antibody; in certain embodiments, a fragment binds to the antigen with a comparable affinity to that of the parent antibody and/or competes with the parent antibody for binding to the antigen. Examples of antigen binding fragments of an antibody include, but are not limited to, Fab fragment, Fab' fragment, F(ab')2 fragment, scFv fragment, Fv fragment, dsFv diabody, dAb fragment, Fd' fragment, Fd fragment, and an isolated complementarity determining region (CDR) region. An antigen binding fragment of an antibody may be produced by any means. For example, an antigen binding fragment of an antibody may be enzymatically or chemically produced by fragmentation of an intact antibody and/or it may be recombinantly produced from a gene encoding the partial antibody sequence. Alternatively or additionally, antigen binding fragment of an antibody may be wholly or partially synthetically produced. An antigen binding fragment of an antibody may optionally comprise a single chain antibody fragment. Alternatively or additionally, an antigen binding fragment of an antibody may comprise multiple chains which are linked together, for example, by disulfide linkages. An antigen binding fragment of an antibody may optionally comprise a multimolecular complex. A functional single domain antibody fragment is in a range from about 5 kDa to about 25 kDa, e.g., from about 10 kDa to about 20 kDa, e.g., about 15 kDa; a functional single-chain fragment is from about 10 kDa to about 50 kDa, e.g., from about 20 kDa to about 45 kDa, e.g., from about 25 kDa to about 30 kDa; and a functional fab fragment is from about 40 kDa to about 80 kDa, e.g., from about 50 kDa to about 70 kDa, e.g., about 60 kDa.

"Associated": As used herein, the term "associated" typically refers to two or more entities in physical proximity with one another, either directly or indirectly (e.g., via one or more additional entities that serve as a linking agent), to form a structure that is sufficiently stable so that the entities remain in physical proximity under relevant conditions, e.g., physiological conditions. In some embodiments, associated moieties are covalently linked to one another. In some embodiments, associated entities are non-covalently linked. In some embodiments, associated entities are linked to one another by specific non-covalent interactions (i.e., by interactions between interacting ligands that discriminate between their interaction partner and other entities present in the context of use, such as, for example streptavidin/avidin interactions, antibody/antigen interactions, etc.). Alternatively or additionally, a sufficient number of weaker non-covalent interactions can provide sufficient stability for moieties to remain associated. Exemplary non-covalent interactions include, but are not limited to, electrostatic interactions, hydrogen bonding, affinity, metal coordination, physical adsorption, host-guest interactions, hydrophobic interactions, pi stacking interactions, van der Waals interactions, magnetic interactions, electrostatic interactions, dipole-dipole interactions, etc.

"Agent": The term "agent" refers to a compound or entity of any chemical class including, for example, polypeptides, nucleic acids, saccharides, lipids, small molecules, metals, or combinations thereof. In certain embodiments, the nanoparticle compositions described herein comprise, have attached, or have associated therewith one or more agents. As will be clear from context, in some embodiments, an agent can be or comprise a cell or organism, or a fraction, extract, or component thereof. In some embodiments, an agent is or comprises a natural product in that it is found in and/or is obtained from nature. In some embodiments, an agent is or comprises one or more entities that are man-made in that it is designed, engineered, and/or produced through action of the hand of man and/or are not found in nature. In some embodiments, an agent may be utilized in isolated or pure form; in some embodiments, an agent may be utilized in crude form. In some embodiments, potential agents are provided as collections or libraries, for example that may be screened to identify or characterize active agents within them. Some particular embodiments of agents that may be utilized include small molecules, antibodies, antibody fragments, aptamers, siRNAs, shRNAs, DNA/RNA hybrids, antisense oligonucleotides, ribozymes, peptides, peptide mimetics, peptide nucleic acids, small molecules, etc. In some embodiments, an agent is or comprises a polymer. In some embodiments, an agent contains at least one polymeric moiety. In some embodiments, an agent comprises a therapeutic, diagnostic and/or drug.

"Biocompatible": The term "biocompatible", as used herein is intended to describe materials that do not elicit a substantial detrimental response in vivo. In certain embodiments, the materials are "biocompatible" if they are not toxic to cells. In certain embodiments, materials are "biocompatible" if their addition to cells in vitro results in less than or equal to 20% cell death, and/or their administration in vivo does not induce inflammation or other such adverse effects. In certain embodiments, materials are biodegradable.

"Biodegradable": As used herein, "biodegradable" materials are those that, when introduced into cells, are broken down by cellular machinery (e.g., enzymatic degradation) or by hydrolysis into components that cells can either reuse or dispose of without significant toxic effects on the cells. In certain embodiments, components generated by breakdown of a biodegradable material do not induce inflammation and/or other adverse effects in vivo. In certain embodiments, biodegradable materials are enzymatically broken down. Alternatively or additionally, in certain embodiments, biodegradable materials are broken down by hydrolysis. In certain embodiments, biodegradable polymeric materials break down into their component polymers. In certain embodiments, breakdown of biodegradable materials (including, for example, biodegradable polymeric materials) includes hydrolysis of ester bonds. In certain embodiments, breakdown of materials (including, for example, biodegradable polymeric materials) includes cleavage of urethane linkages.

"Cancer": As used herein, the term "cancer" refers to a malignant neoplasm or tumor (Stedman's Medical Dictionary, 25th ed.; Hensly ed.; Williams & Wilkins: Philadelphia, 1990). Exemplary cancers include, but are not limited to, brain cancer (e.g., meningioma, glioblastomas, glioma (e.g., astrocytoma, oligodendroglioma), medulloblastoma), prostate cancer, melanoma, breast cancer, gynecological malignancies, colorectal cancers.

"Carrier": As used herein, "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin. In certain embodiments, compositions described herein (e.g., compositions administered to a subject, e.g., compositions comprising a nanoparticle described herein) comprise a carrier.

"Detector": As used herein, the term "detector" includes any detector of electromagnetic radiation including, but not limited to, CCD camera, photomultiplier tubes, photodiodes, and avalanche photodiodes.

"Fluorescent dye": In certain embodiments, the nanoparticle composition comprises or has a nanoparticle with an attached a fluorescent dye comprising one or more fluorophores. Fluorophores comprise fluorochromes, fluorochrome quencher molecules, any organic or inorganic dyes, metal chelates, or any fluorescent enzyme substrates, including protease activatable enzyme substrates. In certain embodiments, fluorophores comprise long chain carbophilic cyanines. In other embodiments, fluorophores comprise DiI, DiR, DiD, and the like. Fluorochromes comprise far red, and near infrared fluorochromes (NIRF). Fluorochromes include but are not limited to a carbocyanine and indocyanine fluorochromes. In certain embodiments, imaging agents comprise commercially available fluorochromes including, but not limited to Cy5.5, Cy5 and Cy7 (GE Healthcare); AlexaFlour660, AlexaFlour680, AlexaFluor750, and AlexaFluor790 (Invitrogen); VivoTag680, VivoTag-S680, and VivoTag-5750 (VisEn Medical); Dy677, Dy682, Dy752 and Dy780 (Dyomics); DyLight547, DyLight647 (Pierce); HiLyte Fluor 647, HiLyte Fluor 680, and HiLyte Fluor 750 (AnaSpec); IRDye 800CW, IRDye 800RS, and IRDye 700DX (Li-Cor); methylene blue; and ADS780WS, ADS830WS, and ADS832WS (American Dye Source) and Kodak X-SIGHT 650, Kodak X-SIGHT 691, Kodak X-SIGHT 751 (Carestream Health).

"In vitro": The term "in vitro" as used herein refers to events that occur in an artificial environment, e.g., in a test tube or reaction vessel, in cell culture, etc., rather than within a multi-cellular organism.

"In vivo": As used herein "in vivo" refers to events that occur within a multi-cellular organism, such as a human and a non-human animal. In the context of cell-based systems, the term may be used to refer to events that occur within a living cell (as opposed to, for example, in vitro systems).

"Imaging agent": The term "imaging agent" as used herein refers to any element, molecule, functional group, compound, fragments thereof or moiety that facilitates detection of an agent (e.g., a polysaccharide nanoparticle) to which it is joined. In certain embodiments, the nanoparticle compositions described herein comprise, have attached, and/or have associated therewith one or more imaging agents. Examples of imaging agents include, but are not limited to: various ligands, radionuclides (e.g., $^{3}$H, $^{14}$C, $^{18}$F, $^{19}$F, $^{32}$P, $^{35}$S, $^{135}$I, $^{125}$I, $^{123}$I, $^{64}$Cu, $^{187}$Re, $^{111}$In, $^{90}$Y, $^{99m}$Tc, $^{177}$Lu, $^{89}$Zr etc.), fluorescent dyes (for specific exemplary fluorescent dyes, see below), chemiluminescent agents (such as, for example, acridinum esters, stabilized dioxetanes, and the like), bioluminescent agents, spectrally resolvable inorganic fluorescent semiconductors nanocrystals (i.e., quantum dots), metal nanoparticles (e.g., gold, silver, copper, platinum, etc.) nanoclusters, paramagnetic metal ions, enzymes (for specific examples of enzymes, see below), colorimetric labels (such as, for example, dyes, colloidal gold, and the like), biotin, dioxigenin, haptens, and proteins for which antisera or monoclonal antibodies are available.

"Image": The term "image", as used herein, is understood to mean a visual display or any data representation that may be interpreted for visual display. For example, a three-dimensional image may include a dataset of values of a given quantity that varies in three spatial dimensions. A three-dimensional image (e.g., a three-dimensional data representation) may be displayed in two-dimensions (e.g., on a two-dimensional screen, or on a two-dimensional printout). In certain embodiments, the term "image" may refer to, for example, to a multi-dimensional image (e.g., a multi-dimensional (e.g., four dimensional) data representation) that is displayed in two-dimensions (e.g., on a two-dimensional screen, or on a two-dimensional printout). The term "image" may refer, for example, to an optical image, an x-ray image, an image generated by: positron emission tomography (PET), magnetic resonance, (MR) single photon emission computed tomography (SPECT), and/or ultrasound, and any combination of these.

"Nanoparticle": As used herein, the term "nanoparticle" refers to a particle having a diameter of less than 1000 nanometers (nm). In some embodiments, a nanoparticle has a diameter of less than 300 nm, as defined by the National Science Foundation. In some embodiments, a nanoparticle has a diameter of less than 100 nm as defined by the National Institutes of Health. In some embodiments, the nanoparticle (inclusive of any ligands or other attached or associated species), is no greater than about 50 nm in diameter (e.g., no greater than 20 nm, e.g., no greater than about 15 nm, e.g., no greater than about 10 nm). In some embodiments, nanoparticles are micelles in that they comprise an enclosed compartment, separated from the bulk solution by a micellar membrane, typically comprised of amphiphilic entities which surround and enclose a space or compartment (e.g., to define a lumen). In some embodiments, a micellar membrane is comprised of at least one polymer, such as for example a biocompatible and/or biodegradable polymer.

"Peptide" or "Polypeptide": The term "peptide" or "polypeptide" refers to a string of at least two (e.g., at least three) amino acids linked together by peptide bonds. In certain embodiments, a polypeptide comprises naturally-occurring amino acids; alternatively or additionally, in certain embodiments, a polypeptide comprises one or more non-natural amino acids (i.e., compounds that do not occur in nature but that can be incorporated into a polypeptide chain; see, for example, http://www.cco.caltech.edu/~dadgrp/Unnatstruct-.gif, which displays structures of non-natural amino acids that have been successfully incorporated into functional ion channels) and/or amino acid analogs as are known in the art may alternatively be employed). In certain embodiments, one or more of the amino acids in a protein may be modified, for example, by the addition of a chemical entity such as a carbohydrate group, a phosphate group, a farnesyl group, an isofarnesyl group, a fatty acid group, a linker for conjugation, functionalization, or other modification, etc.

"Protein": As used herein, the term "protein" refers to a polypeptide (i.e., a string of at least 3-5 amino acids linked to one another by peptide bonds). Proteins may include moieties other than amino acids (e.g., may be glycoproteins, proteoglycans, etc.) and/or may be otherwise processed or modified. In certain embodiments "protein" can be a complete polypeptide as produced by and/or active in a cell (with or without a signal sequence); in certain embodiments, a "protein" is or comprises a characteristic portion such as a polypeptide as produced by and/or active in a cell. In certain embodiments, a protein includes more than one polypeptide chain. For example, polypeptide chains may be linked by one or more disulfide bonds or associated by other means. In certain embodiments, proteins or polypeptides as described herein may contain L-amino acids, D-amino acids, or both, and/or may contain any of a variety of amino acid modifications or analogs known in the art. Useful modifications include, e.g., terminal acetylation, amidation, methylation, etc. In certain embodiments, proteins or polypeptides may comprise natural amino acids, non-natural amino acids, synthetic amino acids, and/or combinations thereof. In certain embodiments, proteins are or comprise antibodies, antibody polypeptides, antibody fragments, biologically active portions thereof, and/or characteristic portions thereof.

"Pharmaceutical composition": As used herein, the term "pharmaceutical composition" refers to an active agent, formulated together with one or more pharmaceutically acceptable carriers. In certain embodiments, active agent is present in unit dose amount appropriate for administration in a therapeutic regimen that shows a statistically significant probability of achieving a predetermined therapeutic effect when administered to a relevant population. In certain embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

"Radiolabel": As used herein, "radiolabel" refers to a moiety comprising a radioactive isotope of at least one element. Exemplary suitable radiolabels include but are not limited to those described herein. In certain embodiments, a radiolabel is one used in positron emission tomography (PET). In certain embodiments, a radiolabel is one used in single-photon emission computed tomography (SPECT). In certain embodiments, radioisotopes comprise $^{99m}$Tc, $^{111}$In, $^{64}$Cu, $^{67}$Ga, $^{186}$Re, $^{188}$Re, $^{153}$Sm, $^{177}$Lu, $^{67}$Cu, $^{123}$I, $^{124}$I, $^{125}$I, $^{11}$C, $^{13}$N, $^{15}$O, $^{18}$F, $^{186}$Re, $^{188}$Re, $^{153}$Sm, $^{166}$Ho, $^{177}$Lu, $^{149}$Pm, $^{90}$Y, $^{213}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{67}$Cu, $^{105}$Rh, $^{111}$Ag, $^{89}$Zr, $^{225}$Ac, and $^{192}$Ir.

"Sensor": As used herein, the term "sensor" includes any sensor of electromagnetic radiation including, but not limited to, CCD camera, photomultiplier tubes, photodiodes, and avalanche photodiodes, unless otherwise evident from the context.

"Subject": As used herein, the term "subject" includes humans and mammals (e.g., mice, rats, pigs, cats, dogs, and horses). In many embodiments, subjects are mammals, particularly primates, especially humans. In certain embodiments, subjects are livestock such as cattle, sheep, goats, cows, swine, and the like; poultry such as chickens, ducks, geese, turkeys, and the like; and domesticated animals particularly pets such as dogs and cats. In certain embodiments (e.g., particularly in research contexts) subject mammals will be, for example, rodents (e.g., mice, rats, hamsters), rabbits, primates, or swine such as inbred pigs and the like. In some embodiments a human subject is an adult, adolescent, or pediatric subject. In some embodiments, a subject is suffering from a disease, disorder or condition, e.g., a disease, disorder or condition that can be treated as provided herein, e.g., a cancer or a tumor listed herein. In some embodiments, a subject is susceptible to a disease, disorder, or condition; in some embodiments, a susceptible subject is predisposed to and/or shows an increased risk (as compared to the average risk observed in a reference subject or population) of developing the disease, disorder or condition. In some embodiments, a subject displays one or more symptoms of a disease, disorder or condition. In some embodiments, a subject does not display a particular symptom (e.g., clinical manifestation of disease) or characteristic of a disease, disorder, or condition. In some embodiments, a subject does not display any symptom or characteristic of a disease, disorder, or condition. In some embodiments, a subject is a patient. In some embodiments, a subject is an individual to whom diagnosis and/or therapy is and/or has been administered.

"Substantially": As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

"Targeting agent": Non-limiting examples of nanoparticle compositions comprising targeting agents (e.g., ligands attached to nanoparticles that cause the nanoparticle compositions to accumulate in or near (and/or be driven to) a particular cell type, tissue type, analyte, or other target) include, for example, a targeting peptide, or antibody fragment. In certain embodiments, the nanoparticle compositions described herein comprise one or more targeting agents. In certain embodiments, the targeting agent comprises a targeting peptide (e.g., RGD, e.g., cRGD, e.g., an analog of RGD, e.g., alphaMSH, e.g., any peptide known to be immunomodulatory and anti-inflammatory in nature). In certain embodiments, the targeting agent comprises an antibody fragment, e.g., wherein the antibody fragment is in a range from about 5 kDa to about 25 kDa (e.g., from about 10 kDa to about 20 kDa, e.g., about 15 kDa) (e.g., wherein the antibody fragment comprises a functional single domain antibody fragment). In certain embodiments, the targeting agent comprises an antibody fragment, and wherein the antibody fragment is from about 20 kDa to about 45 kDa (e.g., from about 25 kDa to about 30 kDa) (e.g., wherein the antibody fragment comprises a functional single chain antibody fragment). In certain embodiments, the targeting agent comprises an antibody fragment, and wherein the antibody fragment is from about 40 kDa to about 80 kDa (e.g., from about 50 kDa to about 70 kDa, e.g., about 60 kDa) (e.g., wherein the antibody fragment comprises a functional fab fragment).

"Therapeutic agent": As used herein, the phrase "therapeutic agent" refers to any agent that has a therapeutic effect and/or elicits a desired biological and/or pharmacological effect, when administered to a subject. In certain embodiments, the therapeutic agent comprises a drug, e.g., a chemotherapy drug (e.g., sorafenib, paclitaxel, docetaxel, MEK162, etoposide, lapatinib, nilotinib, crizotinib, fulvestrant, vemurafenib, bexorotene, and/or camptotecin).

"Therapeutically effective amount": as used herein, "therapeutically effective amount" refers to an amount that produces the desired effect for which it is administered. In certain embodiments, the term refers to an amount that is sufficient, when administered to a population suffering from or susceptible to a disease, disorder, and/or condition in accordance with a therapeutic dosing regimen, to treat the disease, disorder, and/or condition. In certain embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. In certain embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in certain embodiments, a therapeutically effective amount of a particular agent or therapy may be formulated and/or administered in a single dose. In certain embodiments, a therapeutically effective agent may be formulated and/or administered in a plurality of doses, for example, as part of a dosing regimen.

"Treatment": As used herein, the term "treatment" (also "treat" or "treating") refers to any administration of a substance that partially or completely alleviates, ameliorates, relives, inhibits, delays onset of, reduces severity of, and/or reduces incidence of one or more symptoms, features, and/or causes of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In certain embodiments, treatment may be of a subject who has been diagnosed as suffering from the relevant disease, disorder, and/or condition. In certain embodiments, treatment may be of a subject known to have one or more susceptibility factors that are statistically correlated with increased risk of development of the relevant disease, disorder, and/or condition. In certain embodiments, treatment comprises delivery of therapeutics, including but not limited to, small molecule delivery, radiotherapy, immunotherapy, intrinsic therapeutic properties (e.g., ferroptosis), and particle-driven regulation of the tumor microenvironment. It is noted that ferroptosis is induced by iron and reactive oxygen species, along with other chemical moieties in the tumor microenvironment. In certain embodiments, therapeutics are attached to particles, such as those described herein.

Drawings are presented herein for illustration purposes, not for limitation.

BRIEF DESCRIPTION OF DRAWINGS

The foregoing and other objects, aspects, features, and advantages of the present disclosure will become more apparent and better understood by referring to the following description taken in conduction with the accompanying drawings, in which:

FIGS. 1A-1B show an exemplary laser system that can be used in accordance with an illustrative embodiment of the present disclosure.

FIG. 3 shows a table depicting power density ($mW/cm^2$) and power (mW) output of a laser to achieve a beam diameter of 10 mm and beam area of 0.785 ($cm^2$). Other power densities, laser power, or beam diameters can be used to excite the PDT-active moiety (e.g., Cy5, e.g., methylene blue (MB)) associated with the described nanoparticle compositions.

FIGS. 10-14 depict nanotherapeutic methods and systems using particle-driven photodynamic therapy (PDT), according to illustrative embodiments of the present disclosure.

DETAILED DESCRIPTION

Figure 2:
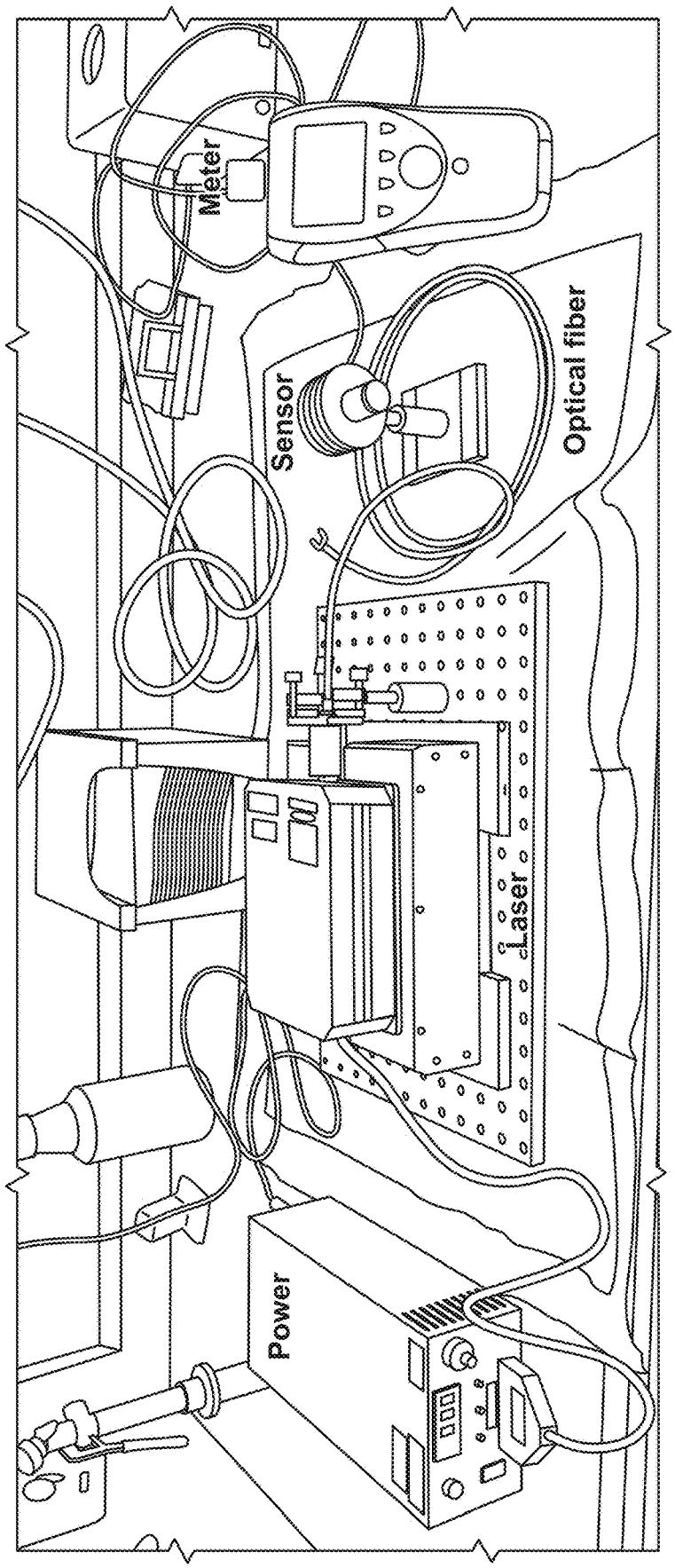
FIG. 2 shows an exemplary setup that can be used in accordance with an illustrative embodiment of the present disclosure.

Throughout the description, where compositions are described as having, including, or comprising specific components, or where methods are described as having, including, or comprising specific steps, it is contemplated that, additionally, there are compositions of the present invention that consist essentially of, or consist of, the recited components, and that there are methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

In certain embodiments, the technology comprises a nanoparticle composition (e.g., an ultrasmall nanoparticle, e.g., a C-dot or other nanoparticle) comprising a PDT-active moiety (e.g., methylene blue or Cy5) that is associated (e.g., covalently bound, e.g., non-covalently bound) to an ultrasmall silica-based nanoparticle. In certain embodiments the PDT-active moiety comprises a fluorophore (e.g., Cy5) that generates higher local concentrations or reactive oxygen species (ROS) at areas requiring treatment (e.g., thereby reducing the power density required for PDT). A photothermal therapy (PTT)-active moiety (e.g., a moiety that absorbs at a longer wavelength than the PDT-active moiety, e.g., 800 nm; e.g., a photosensitive moiety, e.g., a metal nanoparticle, e.g., a gold nanoparticle) can also be attached to the nanoparticle. In certain embodiments, the nanoparticle composition comprises PDT-active-moiety-encapsulated C' dots (e.g., functionalized with immune adjuvants) as described by Kohle et al. in U.S. Provisional Application No. 62/666,086 entitled "Functionalized Sub-10 nm Silica Nanophotosensitizers," filed on May 2, 2018, the disclosure of which is hereby incorporated by reference in its entirety. In certain embodiments, the nanoparticle composition comprises a PDT-active moiety grafted on the surface of the nanoparticle (e.g., in between chains of the stabilizing PEG corona) (e.g., functionalized with immune adjuvants) as described by Kohle et al. in U.S. Provisional Application No. 62/666,086 entitled "Functionalized Sub-10 nm Silica Nanophotosensitizers," filed on May 2, 2018, the disclosure of which is hereby incorporated by reference in its entirety. In certain embodiments, the PDT-active moiety comprises a fluorophore such as methylene blue or Cy5.

In certain embodiments, the described technology comprises a nanoparticle composition as described by Kohle et al. in "Amorphous Quantum Nanomaterials" first published on Dec. 5, 2018 in Advanced Materials, the disclosure of which is hereby incorporated by reference in its entirety. The described single delocalized π-electron dye systems can be isolated in relatively rigid ultra-small (e.g., less than 30 nm in diameter, e.g., less than 20 nm in diameter, e.g., less than 10 nm in diameter) amorphous silica nanoparticles. Chemically tuning the local amorphous silica environment around the dye over a range of compositions provides exquisite control over dye quantum behavior, leading to efficient probes for photodynamic therapy (PDT) and stochastic optical reconstruction microscopy (STORM). Without wishing to be bound to any theory, the described technology provides for efficient fine-tuning of light-induced quantum behavior mediated via effects like spin-orbit coupling can be effectively achieved by systematically varying averaged local environments in glassy amorphous materials as opposed to tailoring well-defined neighboring atomic lattice positions in crystalline solids.

In certain embodiments, silica-based nanoparticles are modified with aluminum as a network hardener and are surface-functionalized with polyethylene glycol (PEG) for colloidal stability in aqueous solution. Chemically tuning the local amorphous silica environment over a range of compositions provides exquisite control over quantum behavior of the π-electron system of the dyes. For example, co-condensing increasing amounts of the heavy element iodine bearing precursors into the ultrasmall silica-based nanoparticles provides control of the strength of spin-orbit coupling to systematically enhance dye intersystem crossing (ISC, i.e., singlet-triplet transition) rates from singlet to triplet quantum states. This provides, for example, highly efficient photosensitizers for applications like photodynamic therapy (PDT). Silica functionalization with increasing numbers of thiol groups enables fine-tuning of light-induced on-off switching of dye dark states providing ultrabright and efficiently blinking nanoprobes for optical super-resolution (SR) microscopy. In certain embodiments, the iodine-containing C' dots are referred to herein as "iC' dots". In certain embodiments, the nanoparticle compositions that can be used for optical super-resolution microscopy are referred to herein as "srC' dots".

In certain embodiments, the nanoparticle composition comprises silica, polymer (e.g., poly(lactic-co-glycolic acid) (PLGA)), biologics (e.g., protein carriers), and/or metal (e.g., gold, iron).

In certain embodiments, the silica-based nanoparticle platform comprises ultrasmall nanoparticles or "C dots," which are fluorescent, organo-silica core shell particles that have diameters controllable down to the sub-10 nm range with a range of modular functionalities. C dots are described by U.S. Pat. No. 8,298,677 B2 "Fluorescent silica-based nanoparticles", U.S. Publication No. 2013/0039848 A1 "Fluorescent silica-based nanoparticles", and U.S. Publication No. US 2014/0248210 A1 "Multimodal silica-based nanoparticles", the contents of which are incorporated herein by reference in their entireties. Incorporated into the silica matrix of the core are near-infrared dye molecules, such as Cy5.5, which provides its distinct optical properties. Surrounding the core is a layer or shell of silica. The silica surface is covalently modified with silyl-polyethylene glycol (PEG) groups to enhance stability in aqueous and biologically relevant conditions. These particles have been evaluated in vivo and exhibit excellent clearance properties owing largely to their size and inert surface. Among the additional functionalities incorporated into C dots are chemical sensing, non-optical (PET) image contrast and in vitro/in vivo targeting capabilities, which enable their use in visualizing lymph nodes for surgical applications, and melanoma detection in cancer.

C or C' dots provide a unique platform for drug delivery due to their physical properties as well as demonstrated human in vivo characteristics. These nanoparticle compositions are ultrasmall and benefit from EPR effects in tumor microenvironments, while retaining desired clearance and pharmacokinetic properties. To this end, in certain embodiments, drug constructs are covalently attached to C dots (or other nanoparticles). C dot-based nanoparticle compositions for drug delivery provide good biostability, minimize premature drug release, and exhibit controlled release of the bioactive compound. In certain embodiments, peptide-based linkers are used for NDC and other applications described herein. These linkers, in the context of antibodies and polymers, are stable both in vitro and in vivo, with highly predictable release kinetics that rely on enzyme catalyzed hydrolysis by lysosomal proteases. For example, cathepsin B, a highly expressed protease in lysosomes, can be utilized to facilitate drug release from macromolecules. By incorporating a short, protease sensitive peptide between the macromolecular backbone and the drug molecule, controlled release of the drug can be obtained in the presence of the enzyme.

In certain embodiments, the nanoparticle is spherical. In certain embodiments, the nanoparticle is non-spherical. In certain embodiments, the nanoparticle is or comprises a material selected from the group consisting of metal/semi-metal/non-metals, metal/semi-metal/non-metal-oxides, -sulfides, -carbides, -nitrides, liposomes, semiconductors, and/or combinations thereof. In certain embodiments, the metal is selected from the group consisting of gold, silver, copper, and/or combinations thereof.

The nanoparticle composition may comprise metal/semi-metal/non-metal oxides including silica ($SiO_2$), titania ($TiO_2$), alumina ($Al_2O_3$), zirconia ($Z_rO_2$), germania ($GeO_2$), tantalum pentoxide ($Ta_2O_5$), $NbO_2$, etc., and/or non-oxides including metal/semi-metal/non-metal borides, carbides, sulfide and nitrides, such as titanium and its combinations (Ti, $TiB_2$, TiC, TiN, etc.).

The nanoparticle compositions described herein allow for generated oxygen species to easily diffuse to and away from the PDT-active moiety. After the nanoparticle compositions have targeted the site of interest and PDT has been performed, the nanoparticle compositions are rapidly cleared from the body via renal clearance to reduce potential side effects. The small hydrodynamic diameters of the nanoparticle compositions allow for the compositions to undergo renal clearance and be rapidly cleared from the body.

In certain embodiments, an ultra-small (e.g., having a diameter less than 50 nm, e.g., having a diameter less than 20 nm, e.g., having a diameter range from 5 nm to 10 nm), was tested in humans as is described in U.S. Publication No. 2014/0248210 A1, which is hereby incorporated by reference in its entirety. In this example, five patients had no adverse events and the agent was well tolerated over the study period. Pharmacokinetic behavior, expressed as the percentage of the injected dose per gram of tissue (% ID/g), versus time post-injection and the corresponding mean organ absorbed doses, were comparable to those found for other commonly used diagnostic radiotracers. Serial PET imaging of this representative patient showed progressive loss of presumed blood pool activity from major organs and tissues, with no appreciable activity seen by 72-hour post-injection (p.i.). Whole-body clearance half-times in these patients were estimated to range from 13-21 hours. Interestingly, there was no notable localization in the liver, spleen, or bone marrow, in contrast to many hydrophobic molecules, proteins, and larger particle platforms (greater than 10 nm). Although patients were pretreated with potassium iodide (KI) to block thyroid tissue uptake, a higher average absorbed thyroid dose was obtained in this patient relative to other tissues. Particles were also primarily excreted by the kidneys, with both kidney and bladder wall (after thyroid and tumor), demonstrating one of the highest % ID/g values by 72 hrs p.i.; as is often the case for renally excreted radiopharmaceuticals, the bladder wall received a higher average absorbed dose than other major organs and tissues. These findings highlight the fact that renal, rather than hepatobiliary, excretion is the predominant route of clearance from the body.

In certain embodiments, the nanoparticle composition comprises an ultrasmall (e.g., sub-50 nm diameter, e.g., sub-20 nm diameter, e.g., sub-15 nm diameter, e.g., sub-10 nm diameter, e.g., sub-8 nm diameter) silica nanoparticle containing a photosensitizing dye (e.g., methylene blue; absorption peak: 645 nm) that is covalently encapsulated within the silica-matrix. In this embodiment, due to the encapsulation of the dye and the specific design on the nanoparticle composition, the singlet oxygen efficiency is dramatically improved (e.g., at least 2-times, e.g., at least 10-times, e.g., at least 50-times, e.g., at least 100-times, e.g., at least 600-times) as compared to the free dye.

In certain embodiments, ligands can be attached to the nanoparticle as described herein. Moreover, a label for imaging and/or radiotherapy can be attached to the nanoparticle as described herein.

In certain embodiments, photodynamic therapy (PDT) can be used in combination with radiotherapy. In certain embodiments, a composition comprising the nanoparticles (e.g., wherein the nanoparticles comprise a radiotherapeutic component) can be administered (e.g., via topical application) to a lesion and treated via radiotherapy. A nanoparticle composition can also be co-administered with a radiotherapeutic composition for combined PDT/radiotherapy. For example, PDT can be combined with radiotherapy in the treatment of disease such as ovarian metastases.

The nanoparticle composition may comprise one or more polymers, e.g., one or more polymers that have been approved for use in humans by the U.S. Food and Drug Administration (FDA) under 21 C.F.R. § 177.2600, including, but not limited to, polyesters (e.g., polylactic acid, poly(lactic-co-glycolic acid), polycaprolactone, polyvalerolactone, poly(1,3-dioxan-2-one)); polyanhydrides (e.g., poly (sebacic anhydride)); polyethers (e.g., polyethylene glycol); polyurethanes; polymethacrylates; polyacrylates; polycyanoacrylates; copolymers of PEG and poly(ethylene oxide) (PEO). In certain embodiments, the diameter of the nanoparticle composition is not substantially increased by the one or more polymers.

The nanoparticle composition may comprise one or more degradable polymers, for example, certain polyesters, polyanhydrides, polyorthoesters, polyphosphazenes, polyphosphoesters, certain polyhydroxyacids, polypropylfumerates, polycaprolactones, polyamides, poly(amino acids), polyacetals, polyethers, biodegradable polycyanoacrylates, biodegradable polyurethanes and polysaccharides. For example, specific biodegradable polymers that may be used include but are not limited to polylysine, poly(lactic acid) (PLA), poly(glycolic acid) (PGA), poly(caprolactone) (PCL), poly (lactide-co-glycolide) (PLG), poly(lactide-co-caprolactone) (PLC), and poly(glycolide-co-caprolactone) (PGC). Another exemplary degradable polymer is poly (beta-amino esters), which may be suitable for use in accordance with the present application.

In certain embodiments, a nanoparticle composition can have or be modified to have one or more functional groups. Such functional groups (within or on the surface of a nanoparticle) can be used for association with any agents (e.g., detectable entities, targeting entities, therapeutic entities, or PEG). In addition to changing the surface charge by introducing or modifying surface functionality, the introduction of different functional groups allows the conjugation of linkers (e.g., (cleavable or (bio-)degradable) polymers such as, but not limited to, polyethylene glycol, polypropylene glycol, PLGA, etc.), targeting/homing agents, and/or combinations thereof.

In certain embodiments, the nanoparticle composition comprises a therapeutic agent, e.g., a drug moiety (e.g., a chemotherapy drug) and/or a therapeutic radioisotope. As used herein, "therapeutic agent" refers to any agent that has a therapeutic effect and/or elicits a desired biological and/or pharmacological effect, when administered to a subject.

For example, the nanoparticle compositions described herein demonstrate enhanced penetration of tumor tissue (e.g., brain tumor tissue) and diffusion within the tumor interstitium, e.g., for treatment of cancer (e.g., gliomas, e.g., high grade gliomas), as described in PCT/US17/30056 ("Compositions and Methods for Targeted Particle Penetration, Distribution, and Response in Malignant Brain Tumors," filed Apr. 28, 2016) by Bradbury et al., the contents of which is hereby incorporated by reference in its entirety. Further described are methods of targeting tumor-associated macrophages, microglia, and/or other cells in a tumor microenvironment using such nanoparticles compositions.

Moreover, diagnostic, therapeutic, and theranostic (diagnostic and therapeutic) platforms featuring such nanoparticle compositions are described for treating targets in both the tumor and surrounding microenvironment, thereby enhancing efficacy of cancer treatment. Use of the nanoparticle compositions described herein with other conventional therapies, including chemotherapy, radiotherapy, immunotherapy, and the like, is also envisaged.

Multi-targeted kinase inhibitors and combinations of single-targeted kinase inhibitors have been developed to overcome therapeutic resistance. Importantly, multimodality combinations of targeted agents, including particle-based compositions designed to carry small molecule inhibitors (SMIs), chemotherapeutics, radiotherapeutic labels, and/or immunotherapies can enhance treatment efficacy and/or improve treatment planning of malignant brain tumors. Coupled with molecular imaging labels, these vehicles permit monitoring of drug delivery, accumulation, and retention, which may, in turn, lead to optimal therapeutic indices.

Moreover, use of radiolabels and/or fluorescent markers attached to (or incorporated in or on, or otherwise associated with) the nanoparticles provide quantitative assessment of nanoparticle composition uptake and monitoring of treatment response. In various embodiments, modular linkers are described for incorporating targeting ligands to develop a drug delivery system with controlled pharmacological properties. The described platforms determine the influence of targeting on nanoparticle composition penetration and accumulation, thereby establishing an adaptable platform for improved delivery of a range of tractable SMIs, for example, to primary and metastatic brain tumors.

In certain embodiments, the nanoparticle composition comprises (e.g., has attached) one or more targeting ligands, e.g., for targeting cancer tissue/cells of interest. In certain embodiments, the nanoparticle composition comprises one or more targeting ligands (e.g., attached thereto), such as, but not limited to, small molecules (e.g., folates, dyes, etc.), aptamers (e.g., A10, AS1411), polysaccharides, small biomolecules (e.g., folic acid, galactose, bisphosphonate, biotin), oligonucleotides, and/or proteins (e.g., (poly)peptides (e.g., αMSH, RGD, octreotide, AP peptide, epidermal growth factor, chlorotoxin, transferrin, etc.), antibodies, antibody fragments, proteins, etc.). In certain embodiments, the nanoparticle composition comprises one or more immune adjuvants (e.g., toll-like receptor agonists, e.g., antibody fragments) (and, optionally, a targeting agent). In certain embodiments, the nanoparticle composition comprises one or more contrast/imaging agents (e.g., fluorescent dyes, (chelated) radioisotopes (SPECT, PET), MR-active agents, CT-agents), and/or therapeutic agents (e.g., small molecule drugs, therapeutic (poly)peptides, therapeutic antibodies, (chelated) radioisotopes, etc.).

In certain embodiments, PET (Positron Emission Tomography) tracers are used as imaging agents. In certain embodiments, PET tracers comprise $^{89}Zr$, $^{64}Cu$, $[^{18}F]$ fluorodeoxyglucose. In certain embodiments, the nanoparticle composition includes these and/or other radiolabels.

In certain embodiments, the nanoparticle composition comprises one or more fluorophores. Fluorophores comprise fluorochromes, fluorochrome quencher molecules, any organic or inorganic dyes, metal chelates, or any fluorescent enzyme substrates, including protease activatable enzyme substrates. In certain embodiments, fluorophores comprise long chain carbophilic cyanines. In other embodiments, fluorophores comprise DiI, DiR, DiD, and the like. Fluorochromes comprise far red, and near infrared fluorochromes (NIRF). Fluorochromes include but are not limited to a carbocyanine and indocyanine fluorochromes. In certain embodiments, imaging agents comprise commercially available fluorochromes including, but not limited to Cy5.5, Cy5 and Cy7 (GE Healthcare); AlexaFlour660, AlexaFlour680, AlexaFluor750, and AlexaFluor790 (Invitrogen); VivoTag680, VivoTag-S680, and VivoTag-S750 (VisEn Medical); Dy677, Dy682, Dy752 and Dy780 (Dyomics); DyLight547, DyLight647 (Pierce); HiLyte Fluor 647, HiLyte Fluor 680, and HiLyte Fluor 750 (AnaSpec); IRDye 800CW, IRDye 800RS, and IRDye 700DX (Li-Cor); methylene blue; and ADS780WS, ADS830WS, and ADS832WS (American Dye Source) and Kodak X-SIGHT 650, Kodak X-SIGHT 691, Kodak X-SIGHT 751 (Carestream Health). In certain embodiments, a multi-wavelength camera as described by Bradbury et al. US Publication No. US 2015/0182118 A1, "Systems, Methods, and Apparatus for Multi-channel Imaging of Fluorescent Sources in Real Time", the disclosure of which is hereby incorporated by reference in its entirety. In certain embodiments, the imaging system used to image the lesion provides both static and functional assessments of the area of treatment (and its surroundings).

In certain embodiments, the fluorophore moiety is Cy5, i.e. Cyanine 5:

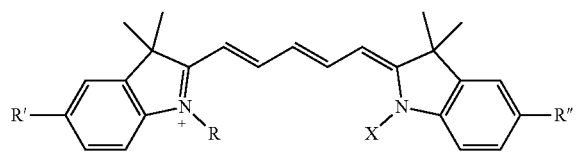

wherein R is —CH$_3$, R' is —H, R" is —H, and X is —(CH$_2$)$_5$—C(O)—, or any suitable salt thereof. In certain embodiments, either or both of R' and R" is —S(O)$_2$—OH or a suitable sulfonate (i.e. —S(O)$_2$—O$^-$) salt thereof. Cy5 can be associated with the described nanoparticle compositions using any suitable means, e.g., conjugation via an activated form of the acid (X is —(CH$_2$)$_5$—C(O)—OH) such as the NHS ester, which can be purchased or can be made using N-hydroxysuccinimide. Other forms of Cy5 can be used in accordance with the systems and methods described by the present disclosure, e.g., equivalents and/or analogues thereof (e.g., any of the foregoing wherein R is —CH$_2$CH$_3$), associated with the described nanoparticle compositions.

In certain embodiments, the fluorophore moiety is Cy5.5, i.e. Cyanine 5.5:

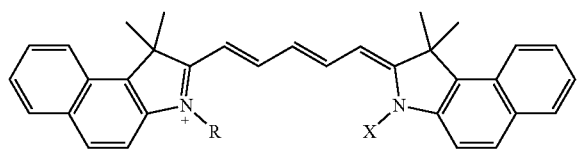

wherein R is —CH$_3$ and X is —(CH$_2$)$_5$—C(O)—, or any suitable salt thereof. Cy5.5 can be associated with the described nanoparticle compositions using any suitable means, e.g., conjugation via an activated form of the acid (X is —(CH$_2$)$_5$—C(O)—OH) such as the NHS ester, which can be purchased or can be made using N-hydroxysuccinimide. Other forms of Cy5.5 can be used in accordance with the systems and methods described by the present disclosure, e.g., equivalents and/or analogues thereof (e.g., R is —CH$_2$CH$_3$), associated with the described nanoparticle compositions.

In certain embodiments, the fluorophore is methylene blue or 3,7-Bis(dimethylamino)phenothiazin-5-ium chloride. In certain embodiments, the fluorophore comprises:

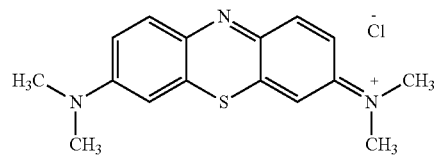

Methylene blue (MB) can be associated with the described nanoparticle compositions using any suitable means, e.g., conjugation via an activated form of the acid (X is —(CH$_2$)$_5$—C(O)—OH) such as the NHS ester, which can be purchased or can be made using N-hydroxysuccinimide. Other forms of methylene blue can be used in accordance with the systems and methods described by the present disclosure, e.g., equivalents and/or analogues thereof, associated with the described nanoparticle compositions.

Functional assessments may include assessment of ROS, oxygenation, perfusion, etc. as described by Bradbury et al., International Application No. PCT/US18/38973 entitled "Systems and Methods for Super-Resolution Optical Imaging Technologies and/or Nanosensor-Driven Patient Monitoring and/or Treatment," filed on Jun. 22, 2018, the contents of which is hereby incorporated by reference in its entirety. For example, functional assessments can utilize nanoparticle compositions (e.g., nanosensors and photoswitchable nanoparticles) that are used to monitor and/or track changes in environmental conditions and/or analytes in the cellular microenvironment before, during, and/or after surgical procedures. Such nanoparticle compositions can detect changes in reactive oxygen species (ROS), pH, pH perturbations, iron levels, calcium, glutathione, and/or amino acids such as leucine, glutamine, arginine, and others, e.g., in the cellular microenvironment. Functional assessments may provide a map of perfusion, perfusion alterations, and/or oxygen/pH status before, during, and/or after surgery. Assessment of analytes may be qualitative or quantitative.

In addition, functional assessments can provide information related to the distribution and/or delivery of photoswitchable nanoparticle compositions at super resolution (e.g., using super-resolution microscopy). For example, distribution and/or delivery of nanoparticle compositions is determined by counting and/or tracking the number of nanoparticles localized within a subcellular compartment, structure, and/or within/across multi-compartments and/or biological barriers (e.g., the blood-brain barrier and/or barriers defining compartments within normal organs, e.g., kidney). The ability to count nanoparticle compositions and localize them within or outside of a cellular compartment, structure, and/or within/across biological barriers at super resolution (i) helps to assess unanticipated events (e.g., effects caused by too little or too many nanoparticles localized within the cell and/or cellular compartment), (ii) can be done patient-bypatient at a cellular level, and (iii) can be coupled with proteomics and/or genomics for improved personalized medicine and care.

Static and functional assessments may inform subsequent treatment and/or an overall treatment plan. An imaging system can be used to direct energy into a small lesion of the oral cavity (or other diseased tissue) to induce cell death (e.g., via apoptosis, ferroptosis, and/or a combination thereof).

Key challenges of PDT probes include reducing toxicity and localizing the PDT probe to a specific site of interest. Singlet oxygen is highly reactive and locally produced by the PDT-active moiety. Typical diffusion lengths of singlet oxygen in tissue before it reacts are on the order of tens of nanometers. Therefore, to minimize damage of healthy tissue, selective targeting is crucial. The described nanoparticle compositions can promote solubility, overcome aggregation in tissues to improve pharmokinetics, and protect PDT-active moieties from enzymatic degradation. Moreover, a nanoparticle composition comprising one or more targeting moieties attached to the nanoparticle reduces systemic side effects, increases the therapeutic concentration of the PDT-active moieties at the target site, and gives room for multi-modality platforms simultaneously allowing for diagnosis, imaging, and treatment.

In certain embodiments, the nanoparticle compositions comprise from 1 to 60 discrete targeting moieties (e.g., of the same type or different types), wherein the targeting moieties bind to receptors on tumor cells (e.g., wherein the nanoparticle compositions have an average diameter no greater than 15 nm, e.g., no greater than 10 nm, e.g., from about 5 nm to about 7 nm, e.g., about 6 nm). In certain embodiments, the 1 to 60 targeting moieties comprises alpha-melanocyte-stimulating hormone (αMSH). In certain embodiments, the nanoparticle compositions comprise a targeting moiety (e.g., αMSH). In certain embodiments, the nanoparticle compositions comprise from 1 to 50 discrete targeting moieties, e.g., from 1 to 30 discrete targeting moieties, e.g., from 1 to 20 discrete targeting moieties, e.g., from 1 to 10 discrete targeting moieties.

Example therapeutics and/or drugs that can be used include RTK inhibitors, such as dasatinib and gefitinib, can target either platelet-derived growth factor receptor (PDGFR) or EGFRmt+ expressed by primary tumor cells of human or murine origin (e.g., genetically engineered mouse models of high-grade glioma, neurospheres from human patient brain tumor explants) and/or tumor cell lines of non-neural origin. Dasatinib and gefitinib analogs can be synthesized to enable covalent attachment to several linkers without perturbing the underlying chemical structure defining the active binding site. In certain embodiments, checkpoint inhibitors can be used as therapeutics and/or drugs for treatment of disease such as cancer.

Cancers that may be treated include, for example, oral cancer, pelvic cancer, prostate cancer, cancer to the oral cavity, tongue cancer, testicular cancer, cervical cancer, lung cancer, colon cancer, renal cancer, head and neck cancer, esophageal cancer, aerodigestive malignancies, and/or leukoplakia.

In certain embodiments, the nanoparticle composition comprises a therapeutic agent, e.g., a drug moiety (e.g., a chemotherapy drug) and/or a therapeutic radioisotope. As used herein, "therapeutic agent" refers to any agent that has a therapeutic effect and/or elicits a desired biological and/or pharmacological effect, when administered to a subject.

The surface chemistry, uniformity of coating (where there is a coating), surface charge, composition, concentration, frequency of administration, shape, and/or size of the nanoparticle composition can be adjusted to produce a desired therapeutic effect.

In certain embodiments, the nanoprobes comprises a chelator, for example, 1,4,8,11-tetraazabicyclo[6.6.2]hexadecane-4,11-diyl)diacetic acid (CB-TE2A); desferoxamine (DFO); diethylenetriaminepentaacetic acid (DTPA); 1,4,7,10-tetraazacyclotetradecane-1,4,7,10-tetraacetic acid (DOTA); thylenediaminetetraacetic acid (EDTA); ethylene glycolbis(2-aminoethyl)-N,N,N',N'-tetraacetic acid (EGTA); 1,4,8,11-tetraazacyclotetradecane-1,4,8,11-tetraacetic acid (TETA); ethylenebis-(2-4 hydroxy-phenylglycine) (EHPG); 5-Cl EHPG; 5Br-EHPG; 5-Me-EHPG; 5t-Bu-EHPG; 5-sec-Bu-EHPG; benzodiethylenetriamine pentaacetic acid (benzo-DTPA); dibenzo-DTPA; phenyl-DTPA, diphenyl-DTPA; benzyl-DTPA; dibenzyl DTPA; bis-2 (hydroxybenzyl)-ethylene-diaminediacetic acid (HBED) and derivatives thereof; Ac-DOTA; benzo-DOTA; dibenzo-DOTA; 1,4,7-triazacyclononane triacetic acid (NOTA); benzo-NOTA; benzo-TETA, benzo-DOTMA, where DOTMA is 1,4,7,10-tetraazacyclotetradecane-1,4,7,10-tetra(methyl tetraacetic acid), benzo-TETMA, where TETMA is 1,4,8,11-tetraazacyclotetradecane-1,4,8,11-(methyl tetraacetic acid); derivatives of 1,3-propylenediaminetetraacetic acid (PDTA); triethylenetetraaminehexaacetic acid (TTHA); derivatives of 1,5,10-N,N',N"-tris(2,3-dihydroxybenzoyl)-tricatecholate (LICAM); and 1,3,5-N,N',N"-tris(2,3-dihydroxybenzoyl)aminomethylbenzene (MECAM), or other metal chelators.

In certain embodiments, the nanoconjugate comprises more than one chelator.

In certain embodiments the radioisotope-chelator pair is $^{89}$Zr-DFO. In certain embodiments the radioisotope-chelator pair Lu-DOTA. In certain embodiments, the is $^{177}$ radioisotope-chelator pair is $^{225}$Ac-DOTA.

In some embodiments, ultrasmall particle compositions may be associated with PET labels and/or optical probes. Nanoparticle compositions may be observed in vivo (e.g., via PET) to evaluate drug accumulation in a target site. For example, nanoparticle compositions with PET labels (e.g., without drug substances) may be administered first. Then, by analyzing the in vivo PET images of the nanoparticle compositions, drug (e.g., conjugated with nanoparticle compositions) concentration and accumulation rate in the tumor may be estimated. The dose may be determined based on the obtained estimation to provide personalized medicine (e.g., tumor size rather than the patient's body weight). In some embodiments, a radiolabeled drug may be traced in vivo. A highly concentrated chemotherapy drug is potentially dangerous if it is not targeted. In some embodiments, nanoparticle compositions with optical probes (e.g., fluorophore) may be used for intraoperative imaging (e.g., where surface of tissue/tumor is exposed) and/or biopsies of tumors.

The nanotherapeutic systems and methods described herein may be tuned by varying the power density of the laser that is directed onto the tissue of the subject, the beam diameter of the laser used, the illumination time of the laser on the tissue of the subject, and/or the fluorophore dye type and concentration of the nanoparticle composition used for PDT treatment. For example, a range of usable power densities and beam diameters of a laser can be determined by directing the laser onto control (healthy) cells to ensure minimal cell death to surrounding healthy tissue, and by experimenting with diseased cells and time-dependent changes in viability post-treatment to ensure satisfactory cell death. This protocol can be used to adjust the variables suitable for different cell types, tumor types, tumor burden, tumor location, achieving minimum viability post-treatment, and type of PDT-active moiety (e.g., fluorophore) that is used in accordance with the embodiments of the present disclosure. Further, the PDT treatment may be combined with ferroptosis, immunotherapy, radiotherapy, and/or photothermal therapy (PTT), as discussed in more detail herein.

In addition, PDT may also be affected by the type of method that is used to administer the described nanoparticle compositions. Lesions, for example, in the oral cavity can be treated topically, while lesions in the pelvis can be treated by directly administering the nanoparticle compositions (e.g., locally) into the intraperitoneal cavity, e.g., for treatment of pelvic spread of disease in the abdomen and pelvis. The nanotherapeutic systems and methods described herein can also be adjusted based on assessment of viability post treatment. The in vitro optimized particle physicochemical properties, laser output parameters, and timing intervals used to assess viability in the examples described herein will inform in vivo protocols.

Constructive Examples

In Vivo PDT Models, Nanoparticle Composition Delivery Methods, and Laser Delivery Methods Tissue that can be treated in accordance with the present disclosure includes oral cavity lesions (e.g., via topical treatment of tongue lesions), metastatic deposits along the lining of the pelvis wall (e.g., via topical or IV treatment), solid ovarian cancer metastases (e.g., along the lining of the pelvis), and/or tissues of the aerodigestive tract (e.g., lips, mouth, tongue, nose, throat, vocal cords, and part of the esophagus and windpipe). Timing between treatments and dose per treatment can be determined using the methods and systems described herein. In certain embodiments, a nanoparticle composition described herein is administered (e.g., topically, e.g., intravenously) to the lesion of interest (e.g., an open cavity). A laser is then directed to the lesion once the nanoparticle compositions are distributed therein.

In one dose surgery, a laser can be administered (e.g., via a camera system) to the lesion. For example, a nanoparticle composition is topically applied to the oral cavity for treatment of diseases such as squamous cell cancer, oral cancer, tongue cancer, cheek cancer, and/or other diseases of the oral cavity. The composition can also be administered to the aerodigestive tract (e.g., lips, mouth, tongue, nose, throat, vocal cords, and part of the esophagus and windpipe) for treatment of aerodigestive malignancies. In certain embodiments, the composition is administered for the treatment of leukoplakia.

Imaging Systems that can be Used for PDT

A LRD-655 Collimated Diode Laser System can be used to perform PDT for small animal studies. The laser power can be from about 0-5 W and delivered via an optical fiber. A Quest Medical Camera System can be used to perform PDT for large animals or human patient studies. Other laser systems, such as other imaging systems described herein, can also be used in the described systems and methods.

In certain embodiments, power density determined by the laser can be used to estimate (and/or inform) what the power density of the camera laser has to be for patient care. Moreover, a camera readout system can be used to display an image of the nanoparticle compositions localized within the tissue (e.g., tissue of the oral cavity), and can supply power for excitation.

In Vitro PDT Cell Lines

FaDu cell lines (human squamous cell carcinoma (SCC) of the hypopharynx) or other oral cavity malignant lesions can be used with the embodiments of the present disclosure. Moreover, precancerous lesions, such as leukoplakia, can be used in accordance with the described systems and methods. Leukoplakia generally refers to a firmly attached white patch on a mucous membrane that is associated with an increased risk of cancer (for example, as described by https://en.wikipedia.org/wiki/Leukoplakia, the disclosure of which is hereby incorporated by reference in its entirety). Leukoplakia can occur in the mouth, although sometimes mucosa in the other parts of the gastrointestinal tract, urinary tract, or genitals may be affected.

Exemplary cell lines include CAL 27, HGF-1, UPCI: SCC154, SCC-4, SCC-9, SCC-25, UM-SCC-103, FT, UPCI, Hs 677.Tg, Fc3Tg, BHY, HSC-3, HN, PE/CA-PJ34 (clone C12), PE/CA-PJ41 (clone D2), COV413B, and COV413A. Other cell lines, such as ovarian cancer lines or other oral cavity cell lines, can also be used in accordance with the described systems and methods.

Small Animal Models for In Vivo PDT

Small animal models can include oral cavity, pelvis, and/or ovarian cancer models for in vivo PDT. In certain embodiments, results obtained from cell lines in vitro may inform small animal model and human clinical studies.

Particle-Driven PDT Combined with Ferroptosis, Immunotherapy, Radiotherapy, and/or photothermal Therapy (PTT) In Vitro or In Vivo Embodiments of the present disclosure are directed to systems and methods for nanotherapies using particle-driven PDT combined with ferroptosis, immunotherapy, radiotherapy, and/or PTT (e.g., for treatment of oral cavity cancer and residual disease, e.g., for treatment of ovarian cancer, e.g., for treatment of malignancies in the aerodigestive tract, e.g., for treatment of metastatic deposits alone the lining of the pelvis wall). Nanoparticle compositions described herein can be topically applied to the aerodigestive tract, oral cavity, and/or along the lining of the pelvis wall. Nanoparticle compositions described herein can also be applied intravenously to the tissue of interest (e.g., pelvis tissue).

Particle-Driven PDT Combined with Ferroptosis

Embodiments of the present disclosure are directed to systems and methods that combine PDT with ferroptosis (which is also ROS-driven). In certain embodiments, the present disclosure describes particle-based PDT with nanoparticle compositions [e.g., comprising nanoparticles that each have a diameter less than 50 nm, e.g., ultrasmall nanoparticles, e.g., C' dots, e.g., methylene blue-encapsulated C' dots ("MB-C' dots")]. In certain embodiments, nanoparticle compositions serve as a reactive oxygen species (ROS) generator of singlet oxygen, which is associated with high cancer cell kill efficiency. In certain embodiments, the nanoparticle compositions are administered to the diseased tissue for accumulation at a sufficiently high concentration for the treatment of the tissue via ferroptosis (e.g., in the presence of a laser). Moreover, in certain embodiments, ROS species can be administered in combination with the nanoparticle compositions as a combinatorial therapeutic (e.g., for the treatment of different lesions).

An example of a general scheme is as follows: (i) design/synthesize nanoparticle compositions comprising functionalized MB-C' dots for the generation of singlet oxygen; (ii) administer the nanoparticle compositions in vitro and/or in vivo; and (iii) analyze resultant antitumor responses (tumor cell death mechanisms, APC activity, and T cell activity) both in vitro and in vivo.

As a first step, the effect of PDT-inducing nanoparticle compositions on cell death via ferroptosis can be determined. Studies can be conducted using a laser system for the generation of singlet oxygen species based on the known physicochemical properties of methylene blue. In certain embodiments, the laser system has one or more lasers, at least one of which has an excitation wavelength (band) within the range from about 630 nm to about 655 nm. ICD-based assays can be used to monitor for exposed calreticulin, secreted ATP, and released HMGB1 in vitro and in vivo; tumor response can be determined using an imaging system described herein.

As a second step, the effect of the nanotherapy on tumor eradication and the prevention of relapse can be assessed. PDT-inducing functionalized MB-C' dots plus singlet oxygen levels can be evaluated in terms of their ability to promote tumor regression and long-term survival in tumor-bearing mice, as well as to promote immunological memory and protection against tumor rechallenge.

In a third step, efficacy of these nanoparticle compositions can be evaluated in the treatment of disseminated disease. The effect of this combination nanotherapy on tumor progression in mice with metachronous tumors can be monitored, wherein the primary tumor is treated with PDT-inducing MB-C'dots, and a distal tumor receives no PDT. The resultant antitumor T cell responses can be evaluated by phenotyping and functional studies. The efficacy of this combinatorial nanotherapeutic regimen using metastatic tumor models (ovarian/GYN and melanoma models) can also be assessed, e.g., with any of the imaging systems described herein.

Particle-Driven PDT Combined with Immunotherapy

Embodiments of the present disclosure are directed to systems and methods that combine PDT with immunotherapy. In certain embodiments, the present disclosure describes particle-based PDT with nanoparticle compositions [e.g., comprising nanoparticles that each have a diameter less than 50 nm, e.g., ultrasmall nanoparticles, e.g., C' dots, e.g., methylene blue-encapsulated C' dots ("MB-C' dots)"].

The nanoparticle compositions can be functionalized with immune adjuvants, such as toll-like receptor (TLR) agonists, and can be systemically administered in combination with checkpoint inhibitors. In certain embodiments, ligands (e.g., immunomodulators) can be attached to the nanoparticle compositions (e.g., for combined immunotherapy). Such a combination approach can potentially circumvent immune evasion/immunomodulatory mechanisms employed by tumors and increase tumor immunogenicity to elicit a multi-antigen vaccination effect without the need for a priori knowledge of tumor antigens.

An example of a general scheme is as follows: (i) design/synthesize nanoparticle compositions comprising functionalized MB-C' dots with TLR agonists; (ii) administer the nanoparticle compositions in vitro and/or in vivo; and (iii) analyze resultant antitumor responses (tumor cell death mechanisms, APC activity, and T cell activity) both in vitro and in vivo.

As a first step, the effect of PDT-inducing nanoparticle compositions, functionalized with TLR agonists (vs no TLR agonists), on immunogenic cell death (ICD) and antigen presentation can be determined. Studies can be conducted using a laser system for the generation of singlet oxygen species based on the known physicochemical properties of methylene blue. In certain embodiments, the laser system has one or more lasers, at least one of which has an excitation wavelength (band) within the range from about 630 nm to about 655 nm. ICD-based assays can be used to monitor for exposed calreticulin, secreted ATP, and released HMGB1 in vitro and in vivo; improved antigen presentation with TLR agonists can be evaluated using an imaging system described herein.

As a second step, the effect of nanoimmunotherapies on tumor eradication and the prevention of relapse can be assessed. PDT-inducing functionalized MB-C' dots plus immune checkpoint inhibitors can be evaluated in terms of their ability to promote tumor regression and long-term survival in tumor-bearing mice (e.g., melanoma, ovarian xenografts), as well as to promote immunological memory and protection against tumor rechallenge.

In a third step, efficacy of these nanoimmunotherapies can be evaluated in the treatment of disseminated disease. The effect of this combination nanoimmunotherapy on tumor progression in mice with metachronous tumors can be monitored, wherein the primary tumor is treated with PDT-inducing MB-C'dots, and a distal tumor receives no PDT. The resultant antitumor T cell responses can be evaluated by phenotyping and functional studies. The efficacy of this combinatorial nanoimmunotherapic regimen using metastatic tumor models (ovarian/GYN and melanoma models) can also be assessed, e.g., with any of the imaging systems described herein.

Particle-Driven PDT Combined with Radiotherapy

Embodiments of the present disclosure are directed to systems and methods that combine PDT with radiotherapy. In certain embodiments, the present disclosure describes particle-based PDT with nanoparticle compositions [e.g., comprising nanoparticles that each have a diameter less than 50 nm, e.g., ultrasmall nanoparticles, e.g., C' dots, e.g., methylene blue-encapsulated C' dots ("MB-C' dots)"]. In certain embodiments, a radiolabel can be associated with the nanoparticle composition for combined radiotherapy and administered to a tissue of a subject. In certain embodiments, a radiotherapeutic composition as described herein can be administered in addition to the nanoparticle composition.

An example of a general scheme is as follows: (i) design/synthesize nanoparticle compositions comprising functionalized MB-C' dots, optionally comprising a radiolabel; (ii) administer the nanoparticle compositions in vitro and/or in vivo; and (iii) analyze resultant antitumor responses (tumor cell death mechanisms, APC activity, and T cell activity) both in vitro and in vivo. In embodiments where a radiolabel is not associated with the nanoparticle particle, a radiotherapeutic composition can be administered separately from the nanoparticle composition.

As a first step, the effect of PDT-inducing nanoparticle compositions on cell death in combination with radiotherapeutic treatment can be assessed. Studies can be conducted using a laser system for the generation of singlet oxygen species based on the known physicochemical properties of methylene blue. In certain embodiments, the laser system has one or more lasers, at least one of which has an excitation wavelength (band) within the range from about 630 nm to about 655 nm. ICD-based assays can be used to monitor for exposed calreticulin, secreted ATP, and released HMGB1 in vitro and in vivo; tumor response can be determined using an imaging system described herein. Radiotherapy is also applied to the diseased tissue, and response can be evaluated.

As a second step, the effect of the nanoradiotherapy on tumor eradication and the prevention of relapse can be assessed. PDT-inducing functionalized MB-C' dots plus radiotherapy can be evaluated in terms of their ability to promote tumor regression and long-term survival in tumor-bearing mice (e.g., melanoma, ovarian xenografts), as well as to promote immunological memory and protection against tumor rechallenge.

In a third step, efficacy of these nanoparticle compositions can be evaluated in the treatment of disseminated disease. The effect of this combination nanoradiotherapy on tumor progression in mice with metachronous tumors can be monitored, wherein the primary tumor is treated with PDT-inducing MB-C'dots, and a distal tumor receives no PDT. The resultant antitumor T cell responses can be evaluated by phenotyping and functional studies. The efficacy of this combinatorial nanotherapeutic regimen using metastatic tumor models (ovarian/GYN and melanoma models) can also be assessed, e.g., with any of the imaging systems described herein.

Particle-Driven PDT Combined with Photothermal Therapy (PTT)

Embodiments of the present disclosure are directed to systems and methods that combine PDT with PTT. In certain embodiments, the present disclosure describes particle-based PDT with nanoparticle compositions [e.g., comprising nanoparticles that each have a diameter less than 50 nm, e.g., ultrasmall nanoparticles, e.g., C' dots, e.g., methylene blue-encapsulated C' dots ("MB-C' dots)" ]. In certain embodiments, a first composition comprising nanoparticles with an attached PDT-active moiety and a second composition with an attached PTT-active moiety are administered to the tissue for combined nanotherapy. In certain embodiments, the first composition comprises nanoparticles, each nanoparticle having an attached PDT-active moiety and a PTT-active moiety for combined treatment. After administering the composition(s), one or more excitation sources (e.g., an infrared camera) are directed to the tissue to treat the disease.

An example of a general scheme is as follows: (i) design/synthesize nanoparticle compositions comprising functionalized MB-C' dots, optionally comprising a PTT-active moiety; (ii) administer the nanoparticle compositions in vitro and/or in vivo; and (iii) analyze resultant antitumor responses (tumor cell death mechanisms, APC activity, and T cell activity) both in vitro and in vivo. In embodiments where a PTT-active moiety is not associated with the nanoparticle particle, a PTT-active composition can be administered separately from the nanoparticle composition.

As a first step, the effect of PDT-inducing nanoparticle compositions on cell death in combination with PTT can be assessed. Studies can be conducted using a laser system for the generation of singlet oxygen species based on the known physicochemical properties of methylene blue. In certain embodiments, the laser system has one or more lasers, at least one of which has an excitation wavelength (band) within the range from about 630 nm to about 655 nm. ICD-based assays can be used to monitor for exposed calreticulin, secreted ATP, and released HMGB1 in vitro and in vivo; tumor response can be determined using an imaging system described herein. Infrared lasers for activating the PTT-active moiety is also applied to the diseased tissue, and response can be evaluated.

As a second step, the effect of the nanotherapy on tumor eradication and the prevention of relapse can be assessed. PDT-inducing functionalized MB-C' dots plus PTT can be evaluated in terms of their ability to promote tumor regression and long-term survival in tumor-bearing mice (e.g., melanoma, ovarian xenografts), as well as to promote immunological memory and protection against tumor rechallenge.

In a third step, efficacy of these nanoparticle compositions can be evaluated in the treatment of disseminated disease. The effect of this combination nanotherapy on tumor progression in mice with metachronous tumors can be monitored, wherein the primary tumor is treated with PDT-inducing MB-C'dots, and a distal tumor receives no PDT. The resultant antitumor T cell responses can be evaluated by phenotyping and functional studies. The efficacy of this combinatorial nanotherapeutic regimen using metastatic tumor models (ovarian/GYN and melanoma models) can also be assessed, e.g., with any of the imaging systems described herein.

Experimental Examples

Detection of Singlet Oxygen Generation

Detection of singlet oxygen ($^1O_2$) was carried out by using 1,3-diphenylisobenzofuran (DPBF) as a chemical $^1O_2$ probe, which reacts irreversibly with $^1O_2$ to cause a decrease in the intensity of the DPBF absorption band at about 400 nm. Measurements were carried out in quartz cuvette in the dark. DPBF in acetonitrile (20 µL, 8 mM) was added to a solution of ultrasmall PDT nanoparticle compositions in acetonitrile (2 mL). The solution was then irradiated with a LRD-655 Collimated Diode Laser System (wavelength: 655 nm). The absorption spectra of the mixture after 655 nm laser irradiation was obtained after given time intervals using a UV/Vis spectrophotometer. Free methylene blue (MB) in acetonitrile mixed with DPBF (20 µL) was introduced as a control group. A relationship between the $^1O_2$ generation efficacy and 655 nm laser power density (or illumination time) can also be studied. The generation (or the presence) of $^1O_2$ can also be detected by using a Singlet Oxygen Sensor Green (SOSG) Reagent, which is a singlet oxygen indicator that initially exhibits weak blue fluorescence (excitation peaks: 372 and 393 nm; emission peaks: 395 and 416 nm), but emits a green fluorescence (excitation/emission: ~504/525 nm) in the presence of singlet oxygen. The generation (or the presence) of $^1O_2$ can also be detected by using the ROS sensor CM-H2DCFDA (which is a chloromethyl derivative of H2DCFDA from Thermofisher, Ex/Em: ~492-495/517-527 nm) (see, e.g., FIGS. 4A-4B). (See also U.S. Provisional Application No. 62/666,086 entitled "Functionalized Sub-10 nm Silica Nanophotosensitizers," filed on May 2, 2018, the disclosure of which is hereby incorporated by reference in its entirety for more information on the nanoparticle composition technology).

In Vitro PDT

For in vitro photodynamic therapy (PDT), cells were seeded into 96-well plates at $5 \times 10^3$/well until adherent and then incubated with series concentrations of PDT nanoparticle compositions (or control groups) for overnight. After the culture medium was replaced with the fresh medium, cells were then irradiated by the 655 nm laser at a selected power density (power density range: zero to 5 W/cm$^2$). The laser illumination time was in the range of 2 min to 20 min. Cells were then incubated at 37° C. under 5% CO$_2$ for an additional 1 to 7 days. Afterwards, a cell viability assay using CellTiter-Glo assay (Promega) was conducted to determine cell viability relative to that found for untreated cells. The in vitro PDT effect can also visualized using confocal imaging and the H2DCFDA (Thermofisher, Ex/Em: ~492-495/517-527 nm) ROS sensor. A living/dead cell staining assay could also be performed by Calcein-AM/Propidium Iodide (PI) staining and imaged on a confocal microscope.

FIGS. 1A-1B show an exemplary laser system that can be used in accordance with an illustrative embodiment of the present disclosure. In this embodiment, the beam size is from about 7 nm to about 8 mm in diameter and covers an area of tissue of about 0.5024 cm². In this embodiment, the laser directs light having a wavelength of 655 nm. Other beam sizes and areas can be used in accordance with the described systems and methods.

FIG. 2 shows an exemplary setup that can be used in accordance with an illustrative embodiment of the present disclosure. This exemplary setup includes a power source, a laser, an optical fiber, a sensor, and a meter.

FIG. 3 shows a table depicting power density (mW/cm²) and power (mW) output of a laser to achieve a beam diameter of 10 mm and beam area of 0.785 (cm²). Other power densities, laser power, or beam diameters can be used to excite the PDT-active moiety (e.g., Cy5, e.g., methylene blue (MB)) associated with the described nanoparticle compositions. In FIG. 3, for example, if beam size is maintained at 10 mm in diameter, an output of at least 4500 mW/cm² at a 655 nm wavelength is needed to excite Cy5 or methylene blue (MB). It is noted that this power density may also change depending on the tissue composition, tumor type, or how the therapy is administered to the tissue.

Figure 4A:
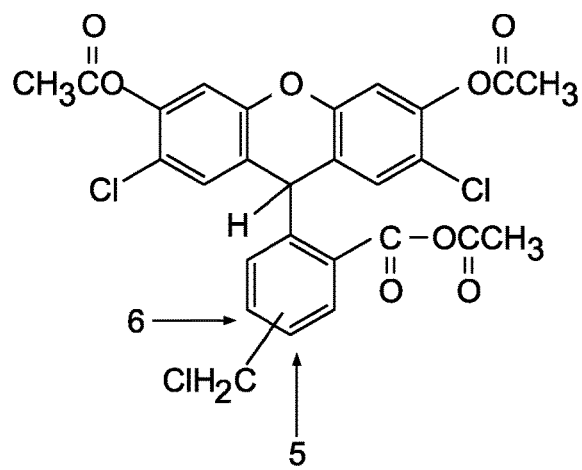
FIGS. 4A-4B show a ROS sensor chemical structure (FIG. 4A) and fluorescence spectra of the ROS sensor (FIG. 4B) that can be used in accordance with an illustrative embodiment of the present disclosure.
Figure 4B:
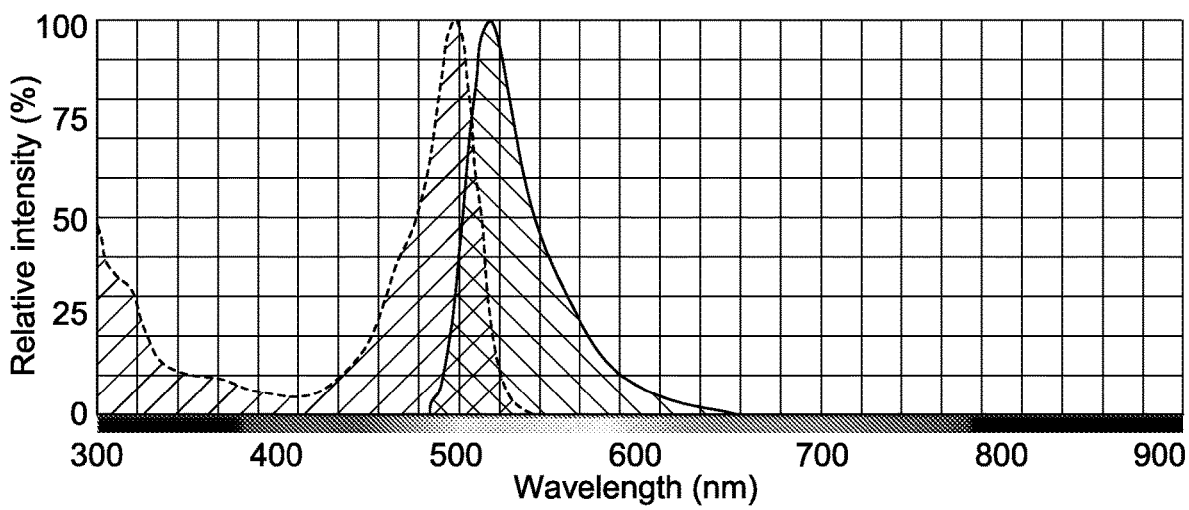

FIGS. 4A-4B show the ROS sensor chemical structure (FIG. 4A) and fluorescence spectra of the ROS sensor (FIG. 4B) that can be used in accordance with an illustrative embodiment of the present disclosure. The ROS sensor (CM-H2DCFDA) shown in FIG. 4A is a chloromethyl derivative of H2DCFDA, and is useful as an indicator for reactive oxygen species (ROS) in cells. This indicator exhibits improved retention in live cells than H2DCFDA. CM-H2DCFDA passively diffuses into cells, where its acetate groups are cleaved by intracellular esterases and its thiol-reactive chloromethyl group reacts with intracellular glutathione and other thiols. Subsequent oxidation yields a fluorescent adduct that is trapped inside the cell, thus facilitating long-term studies. Fluorescence can be monitored using a flow cytometer, fluorometer, microplate reader, or fluorescence microscope, using excitation sources and filters appropriate for fluorescein. Ex/Em: ~492-495/517-527 nm (495 nm/520 nm).

Figure 5:
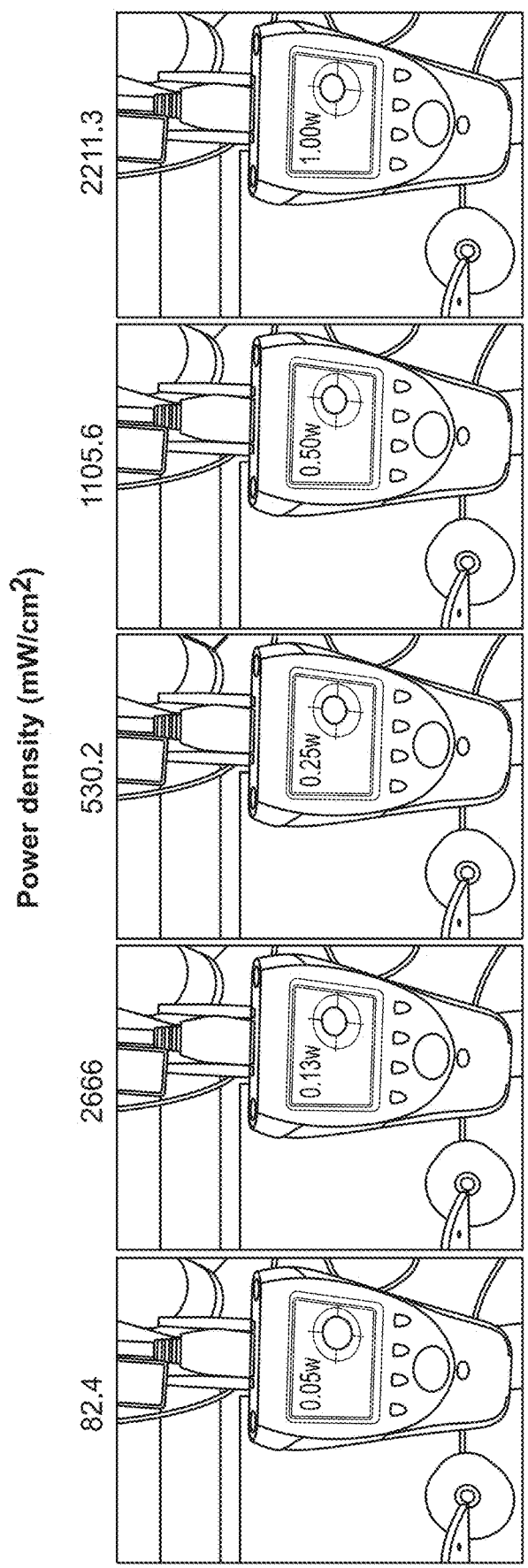
FIG. 5 shows a calibration test that demonstrates that power density (mW/cm2) is dependent on beam area. As power density increases, beam area decreases.

FIG. 5 shows a calibration test that demonstrates that power density (mW/cm²) is dependent on beam area. As power density increases, beam area decreases.

Figure 6A:
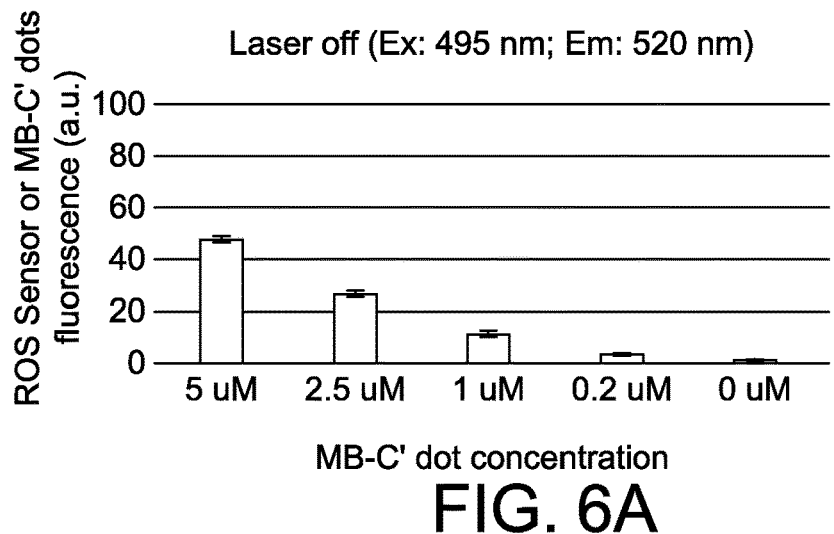
FIGS. 6A-6C represent plots showing concentration-dependent ROS generation using nanoparticle compositions containing methylene blue (or MB-C' dots).
Figure 6B:
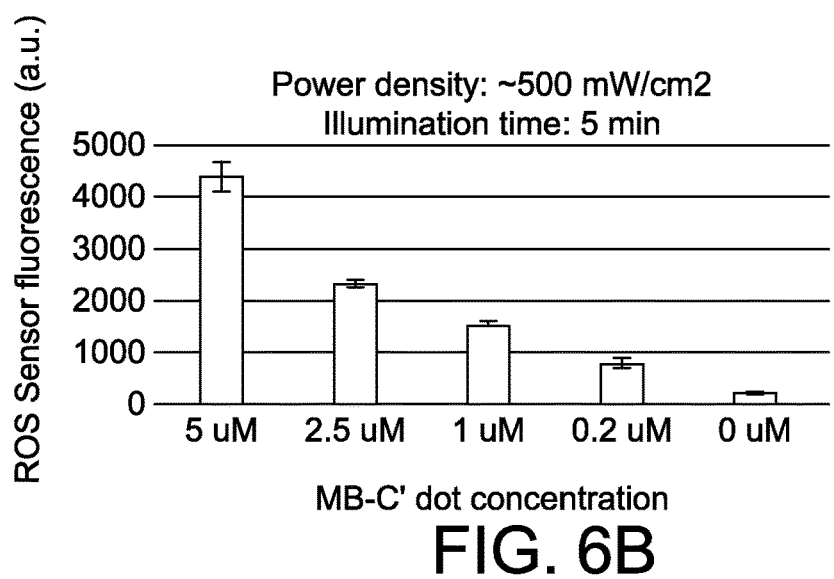
Figure 6C:
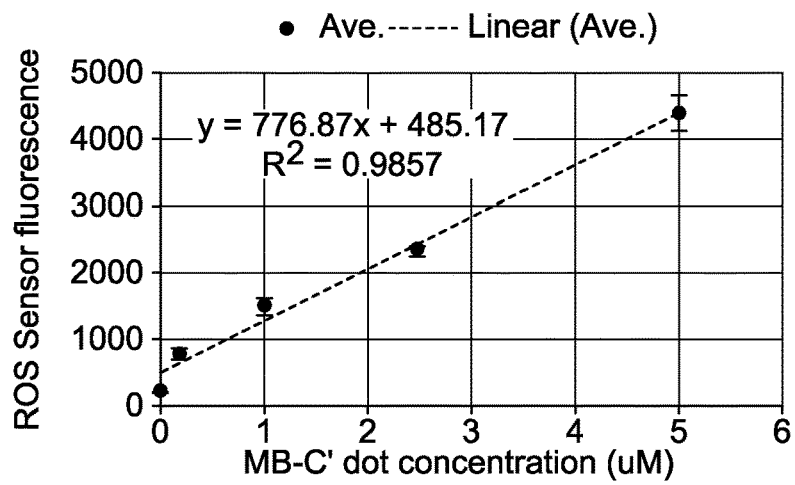

FIGS. 6A-6C represent plots showing concentration-dependent ROS generation using nanoparticle compositions containing methylene blue (or MB-C' dots). Results show that as concentration decreases, ROS generation also decreases. 504 of MB-C' dots of varying concentrations were mixed with 504 of 5 µM solution of ROS sensor. Laser power density was maintained at 500 mW/cm². Illumination time was 5 minutes. (N=3 for each group.)

Figure 7:
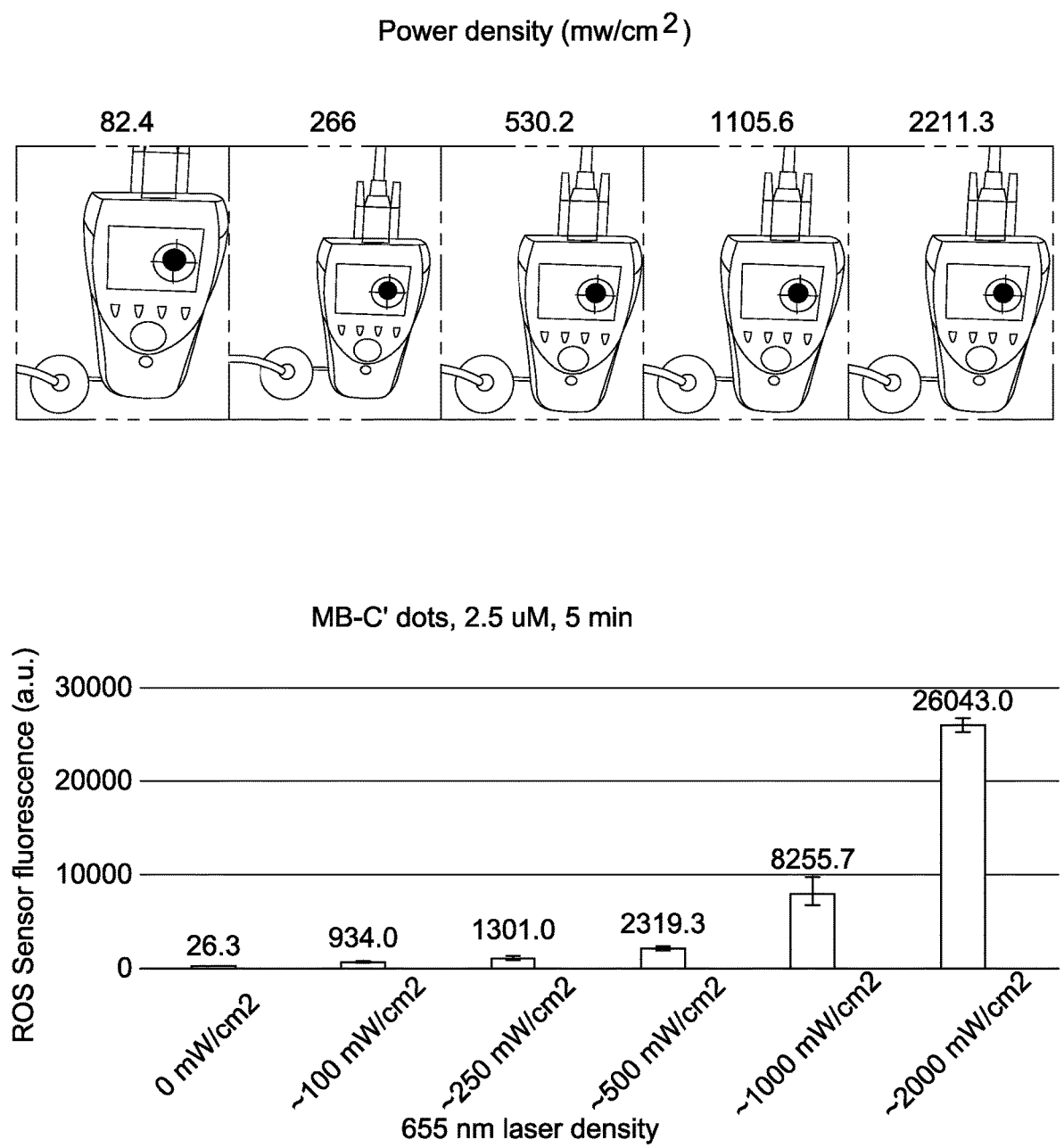
FIG. 7 shows ROS generation of nanoparticle compositions (MB-C' dots).

FIG. 7 shows ROS generation of nanoparticle compositions (MB-C' dots). A high power density of about 2000 mW/cm² generated significant ROS. This data was produced by using a nanoparticle composition concentration of 2.5 µM, and irradiating the compositions for 5 minutes at 655 nm laser excitation across a range of power densities. The results show that ROS generation does not vary linearly with power density. In certain embodiments, alternative fluorophores (other than MB) can be used that may require different irradiation times and/or beam areas, and may produce higher ROS (e.g., see FIG. 9).

Figure 8:
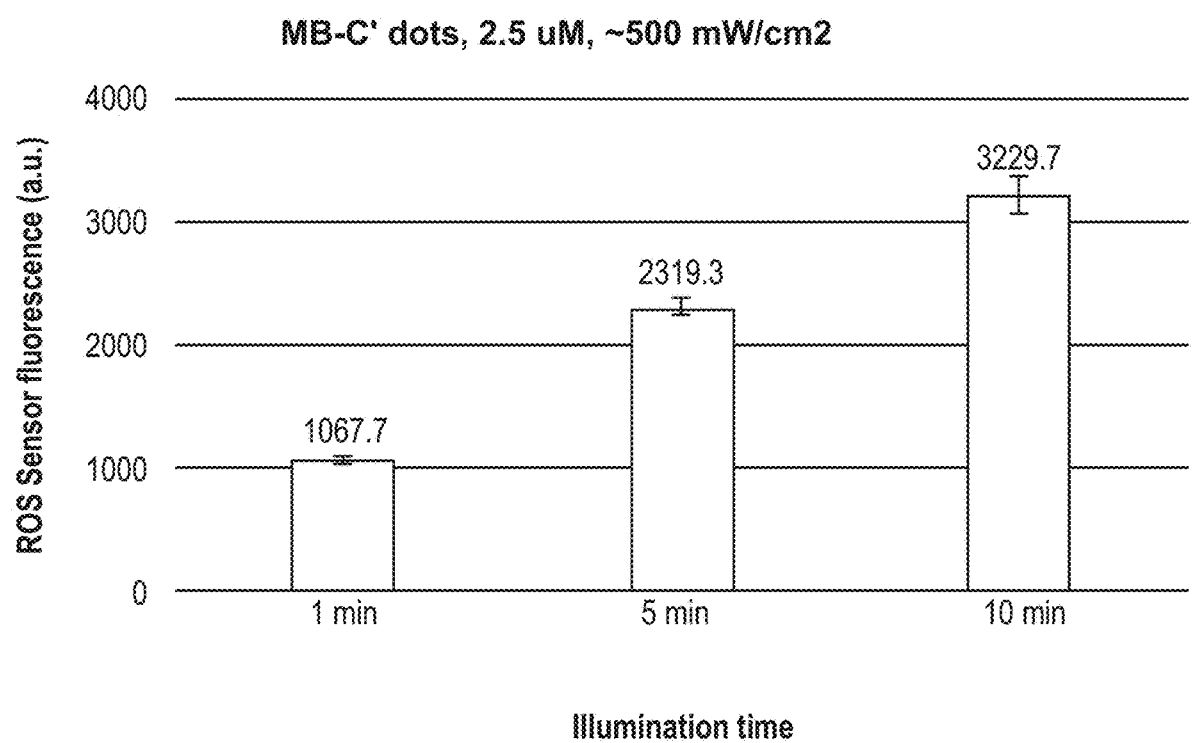
FIG. 8 shows ROS generation as a function of illumination time (1 minute, 5 minutes, 10 minutes).

FIG. 8 shows ROS generation as a function of illumination time (1 minute, 5 minutes, 10 minutes). The results show that an increase in ROS generation occurs at longer illumination times. Nanoparticle compositions (MB-C' dots) were administered at 2.5 µM and illuminated with about 500 mW/cm² power density.

Figure 9:
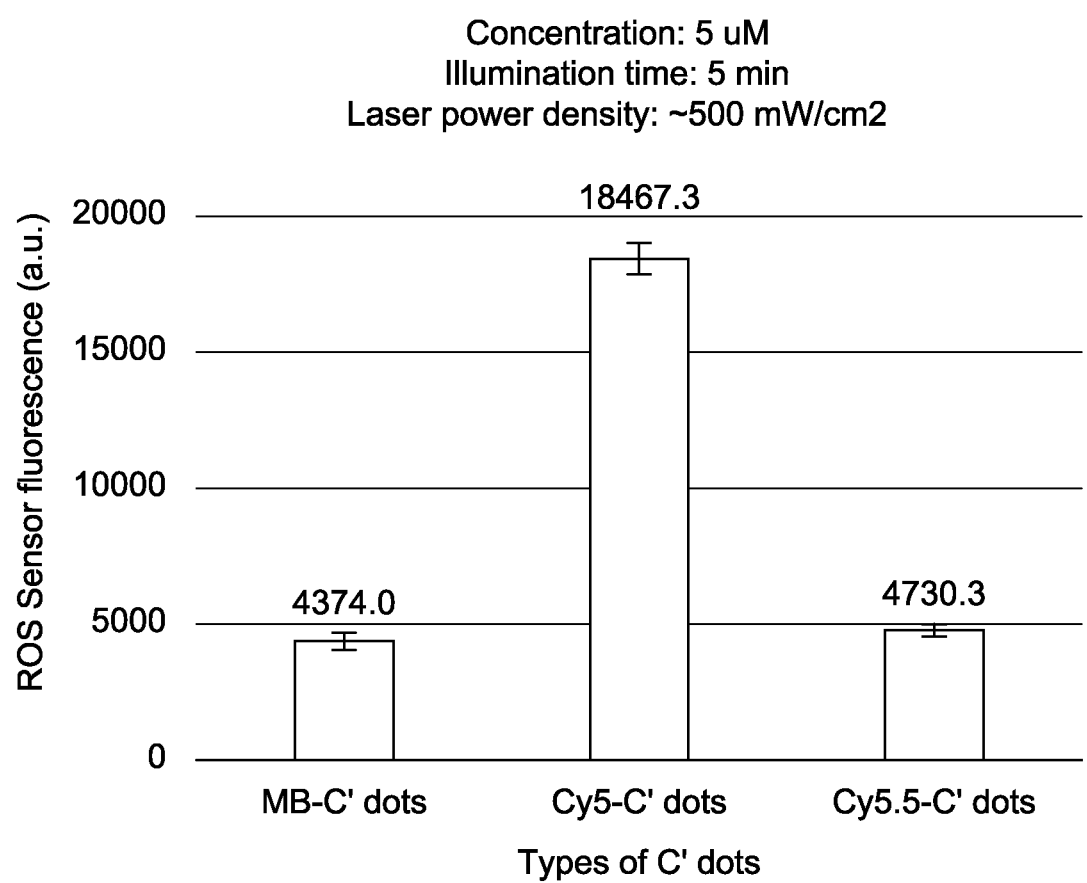
FIG. 9 shows a plot that indicates that different fluorophores generate different levels of ROS. This data shows that Cy5-C' dots produced more ROS than MB-C' dots or Cy5.5-C' dots.
Figure 10:
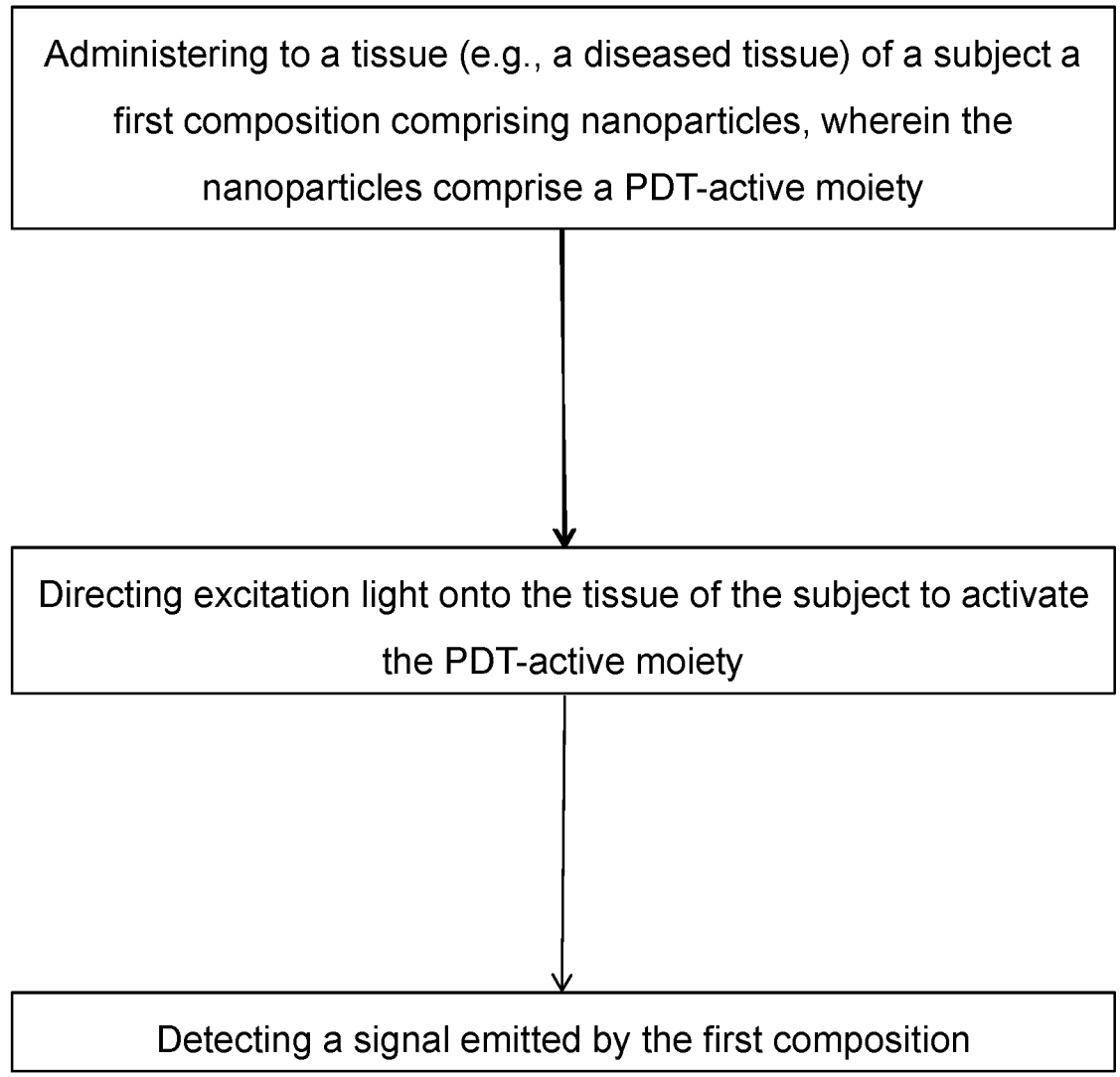
Figure 11:
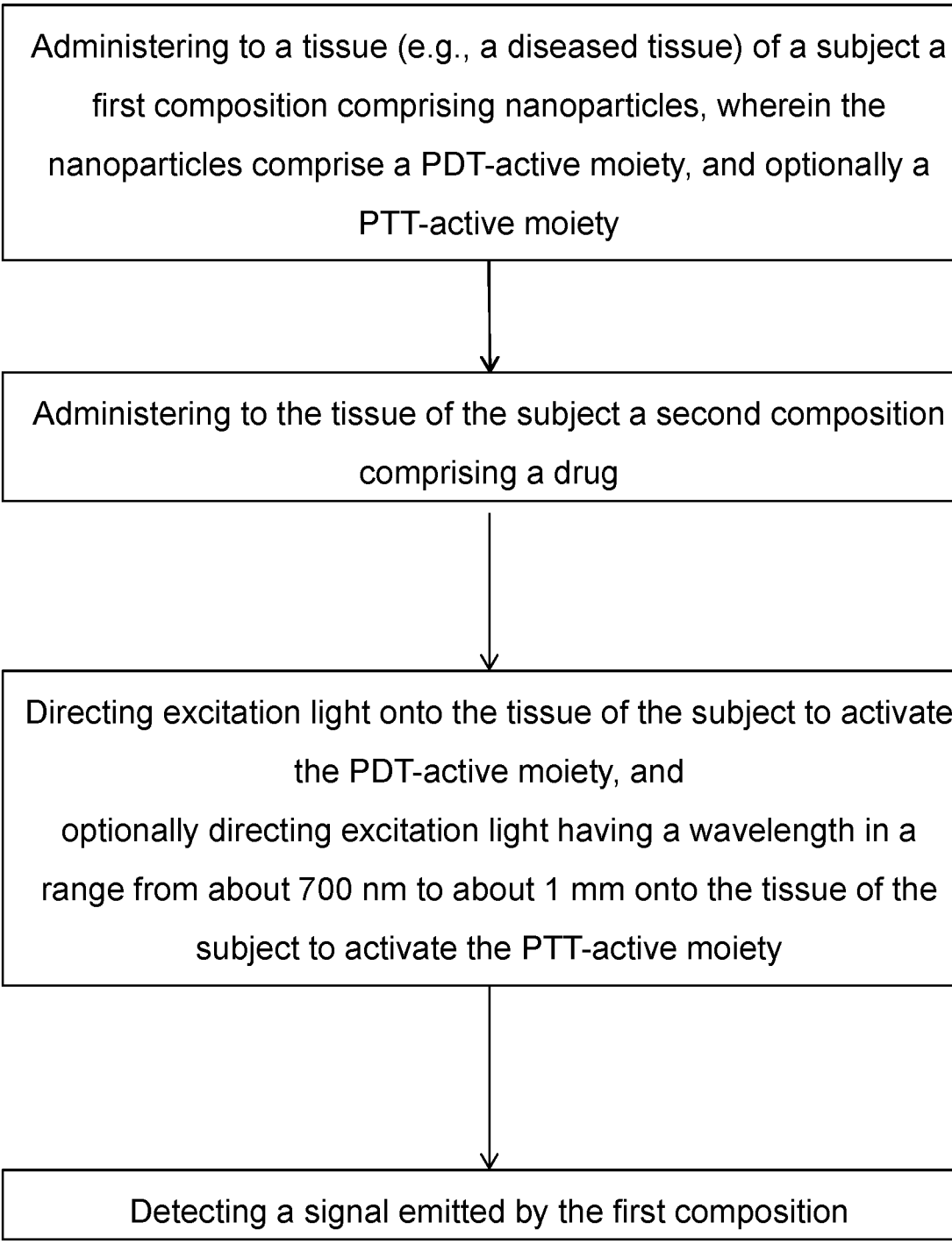
Figure 13:
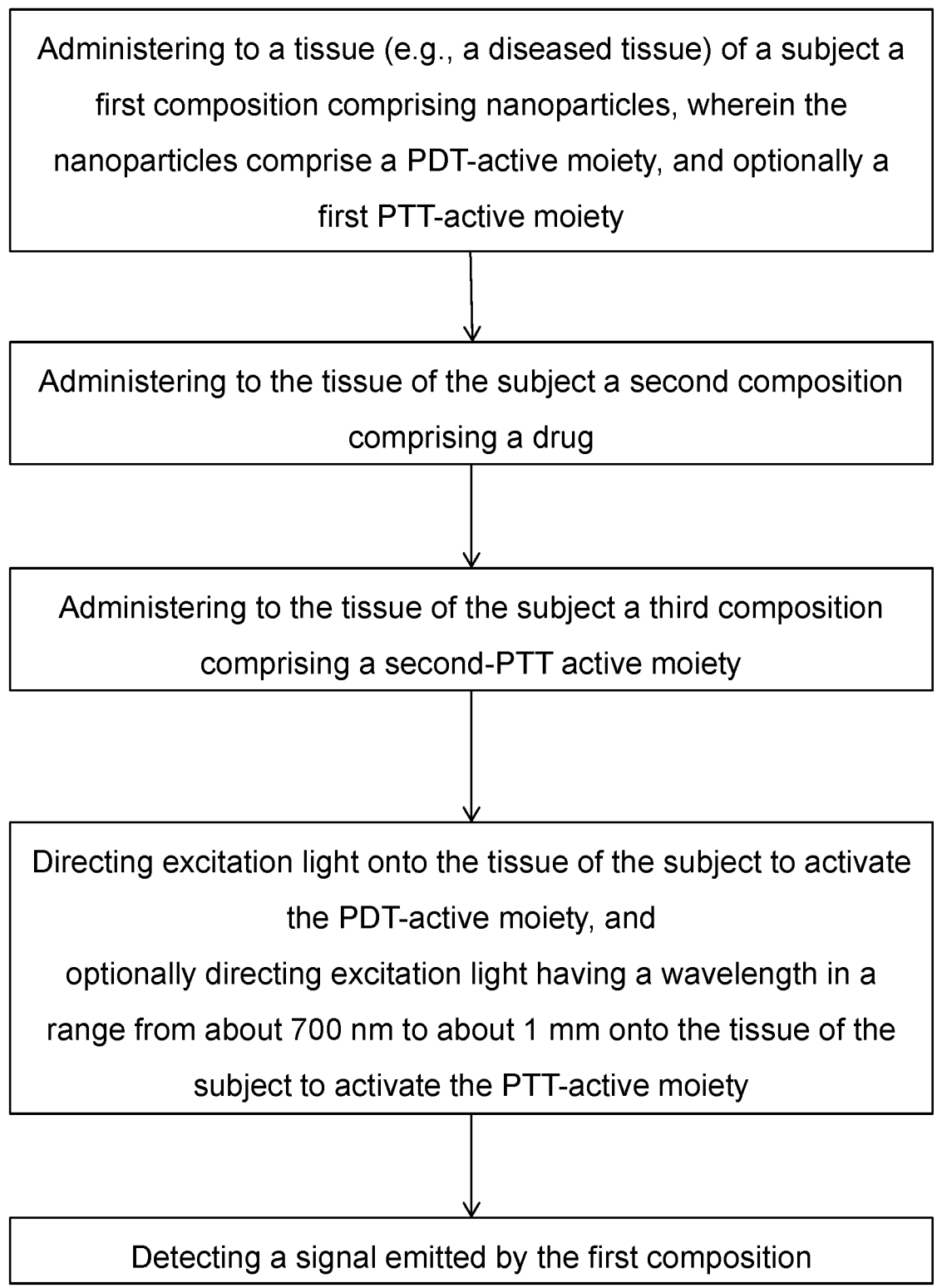

FIG. 9 shows a plot that indicates that different fluorophores generate different levels of ROS. This data shows that Cy5-C' dots produced more ROS than MB-C' dots or Cy5.5-C' dots. It is noted that for Cy5, ROS generation was higher when a higher power density was used.

What is claimed is:

1. A nanotherapeutic method using particle-driven photodynamic therapy (PDT), the method comprising:
   (a) administering to a tissue of a subject a first composition comprising nanoparticles, wherein the nanoparticles have an average diameter no greater than 20 nm, wherein the nanoparticles comprise:
       (i) a PDT-active moiety comprising a PDT-photosensitive agent within the nanoparticle, and
   (b) directing excitation light onto the tissue of the subject to activate the PDT-active moiety; and
   (c) detecting a signal emitted by the first composition.

2. The method of claim 1, wherein the PDT-photosensitive agent comprises a fluorophore.

3. The method of claim 1, wherein the PDT-photosensitive agent comprises methylene blue.

4. The method of claim 1, wherein the PDT-photosensitive agent comprises Cy5.

5. The method of claim 1, wherein the PDT-active moiety absorbs electromagnetic radiation (emr) having a wavelength within a range from about 600 nm to about 700 nm.

6. The method of claim 1, comprising generating a reactive oxygen species (ROS).

7. The method of claim 1, the method comprising:
   administering the first composition to the tissue of the subject for accumulation at sufficiently high concentrations in the tissue to induce ferroptosis.

8. The method of claim 1, the method comprising:
   administering to the tissue of the subject a second composition comprising a drug.

9. The method of claim 8, wherein the drug comprises an immune adjuvant.

10. The method of claim 1, wherein the first composition comprises an immune adjuvant.

11. The method of claim 1, wherein the tissue comprises a member selected from the group consisting of pelvis tissue, aerodigestive tract tissue, mouth tissue, gastrointestinal tract tissue, urinary tract tissue, and genital tissue.

12. The method of claim 1, wherein the method comprises a theranostic method.

13. The method of claim 12, wherein the excitation light that is directed onto the tissue for treatment is directed at a higher power density than the excitation light that is directed onto the tissue for diagnostics.

14. The method of claim 1, wherein the excitation light is directed onto the tissue of the subject via a multichannel camera system for both imaging and PDT treatment.

15. The method of claim 1, wherein a first laser treats the tissue of the subject, and a second laser detects the signal emitted by the first composition.

16. The method of claim 1, wherein the first composition comprises:
   (ii) a first photothermal therapy (PTT)-active moiety.

17. The method of claim 16, the method comprising:
   administering to the tissue of the subject a third composition comprising a second PTT-active moiety.

18. The method of claim 1, the method comprising:
   directing excitation light having a wavelength in a range from about 700 nm to about 1 mm onto the tissue of the subject, thereby treating the tissue with photothermal therapy (PTT).

19. The method of claim 1, the method comprising:
administering radiotherapy to the tissue of the subject.

20. The method of claim 19, wherein the radiotherapy comprises administering a radiotherapeutic composition to the tissue.

21. The method of claim 1, wherein the first composition comprises a radiolabel.

22. The method of claim 1, wherein the nanoparticles are silica-based.

23. The method of claim 1, wherein the nanoparticles comprise:
a silica-based core;
a silica shell surrounding at least a portion of the core; and
an organic polymer attached to the nanoparticle, thereby coating the nanoparticle.

24. The method of claim 1, wherein the first composition further comprises a reactive oxygen species (ROS) sensor.

25. A device for performing the method of claim 1.

* * * * *